(12) United States Patent
Schwartz et al.

(10) Patent No.: US 8,086,315 B2
(45) Date of Patent: Dec. 27, 2011

(54) CARDIAC STIMULATION APPARATUS AND METHOD FOR THE CONTROL OF HYPERTENSION

(75) Inventors: Robert S. Schwartz, Inver Grove Heights, MN (US); Robert A. van Tassel, Excelsior, MN (US)

(73) Assignee: ASAP Medical, Inc., Eden Prairie, MN (US)

( * ) Notice: Subject to any disclaimer, the term of this patent is extended or adjusted under 35 U.S.C. 154(b) by 507 days.

(21) Appl. No.: 12/157,435

(22) Filed: Jun. 10, 2008

(65) Prior Publication Data

US 2009/0018608 A1    Jan. 15, 2009

Related U.S. Application Data

(63) Continuation-in-part of application No. 11/057,279, filed on Feb. 11, 2005, now abandoned.

(60) Provisional application No. 60/544,112, filed on Feb. 12, 2004.

(51) Int. Cl.
*A61N 1/365* (2006.01)
(52) U.S. Cl. .......................... 607/44; 607/23
(58) Field of Classification Search ............. 607/17, 607/23, 44
See application file for complete search history.

(56) References Cited

U.S. PATENT DOCUMENTS

| | | | |
|---|---|---|---|
| 3,814,106 A | 6/1974 | Berkovitz | |
| 4,407,287 A | 10/1983 | Herpers | |
| 4,719,921 A | 1/1988 | Chirife | |
| 4,899,752 A | 2/1990 | Cohen | |
| 5,063,239 A | 11/1991 | Schwenner et al. | |
| 5,163,429 A | 11/1992 | Cohen | |
| 5,213,098 A | 5/1993 | Bennett et al. | |
| 5,318,595 A | 6/1994 | Ferek-Petric et al. | |

(Continued)

FOREIGN PATENT DOCUMENTS

WO    9944682    9/1999

(Continued)

OTHER PUBLICATIONS

Whinnett et al., "Haemodynamic effects of changes in atrioventricular and interventricular delay in cardiac resynchronization therapy show a consistent pattern: analysis of shape, magnitude and relative importance of atrioventricular and interventricular delay", Heart, May 18, 2006, pp. 1628-1634, vol. 96, BMJ Publishing Group and British Cardiovascular Society, published online first.

(Continued)

*Primary Examiner* — Carl H. Layno
*Assistant Examiner* — Tammie K Heller
(74) *Attorney, Agent, or Firm* — Plumsea Law Group, LLC

(57) ABSTRACT

A method that electrically stimulates a heart muscle to alter the ejection profile of the heart, to control the mechanical function of the heart and reduce the observed blood pressure of the patient. The therapy may be invoked by an implantable blood pressure sensor associated with a pacemaker like device. In some cases, where a measured pretreatment blood pressure exceeds a treatment threshold, a patient's heart may be stimulated with an electrical stimulus timed relative to the patient's cardiac ejection cycle. This is done to cause dyssynchrony between at least two cardiac chambers, which alters the patient's cardiac ejection profile from a pretreatment cardiac ejection profile. This has the effect of reducing the patient's blood pressure from the measured pretreatment blood pressure.

22 Claims, 18 Drawing Sheets

U.S. PATENT DOCUMENTS

| | | | |
|---|---|---|---|
| 5,584,868 A | 12/1996 | Salo et al. | |
| 5,601,615 A | 2/1997 | Markowitz et al. | |
| 5,612,380 A | 3/1997 | Lerner et al. | |
| 5,713,928 A | 2/1998 | Bonnet et al. | |
| 5,891,176 A | 4/1999 | Bornzin | |
| 6,271,015 B1 | 8/2001 | Gilula et al. | |
| 6,314,322 B1 | 11/2001 | Rosenberg | |
| 6,450,942 B1 | 9/2002 | Lapanashvili et al. | |
| 6,580,946 B2 | 6/2003 | Struble | |
| 6,628,988 B2 | 9/2003 | Kramer et al. | |
| 6,666,826 B2 | 12/2003 | Salo et al. | |
| 6,668,195 B2 | 12/2003 | Warman et al. | |
| 6,699,682 B2 | 3/2004 | Gilula et al. | |
| 6,795,732 B2 | 9/2004 | Stadler et al. | |
| 6,832,113 B2 | 12/2004 | Belalcazar | |
| 7,001,611 B2 | 2/2006 | Kiso et al. | |
| 7,092,759 B2 | 8/2006 | Nehls et al. | |
| 7,098,233 B2 | 8/2006 | Di Cesare et al. | |
| 7,103,410 B2 | 9/2006 | Kramer et al. | |
| 7,289,849 B2 | 10/2007 | Baynham | |
| 7,346,394 B2 | 3/2008 | Liu et al. | |
| 7,348,173 B2 | 3/2008 | Gilula et al. | |
| 7,548,782 B2 | 6/2009 | Kramer et al. | |
| 7,676,264 B1 | 3/2010 | Pillai et al. | |
| 7,711,420 B2 | 5/2010 | Baynham et al. | |
| 7,725,173 B2 | 5/2010 | Viertio-Oja et al. | |
| 7,725,185 B2 | 5/2010 | Liu et al. | |
| 7,765,008 B2 | 7/2010 | Ben-Haim et al. | |
| 2002/0161410 A1 | 10/2002 | Kramer et al. | |
| 2002/0173826 A1 | 11/2002 | Lincoln et al. | |
| 2003/0060858 A1* | 3/2003 | Kieval et al. | 607/44 |
| 2003/0083700 A1 | 5/2003 | Hill | |
| 2003/0144702 A1 | 7/2003 | Yu et al. | |
| 2003/0144703 A1 | 7/2003 | Yu et al. | |
| 2003/0176896 A1 | 9/2003 | Lincoln et al. | |
| 2004/0015081 A1 | 1/2004 | Kramer et al. | |
| 2004/0049235 A1 | 3/2004 | Deno et al. | |
| 2004/0167410 A1 | 8/2004 | Hettrick | |
| 2004/0186523 A1 | 9/2004 | Florio | |
| 2004/0215255 A1 | 10/2004 | Vries | |
| 2004/0215266 A1* | 10/2004 | Struble et al. | 607/17 |
| 2005/0102002 A1 | 5/2005 | Salo et al. | |
| 2005/0119285 A1 | 6/2005 | Matos et al. | |
| 2005/0149130 A1 | 7/2005 | Libbus | |
| 2005/0222640 A1 | 10/2005 | Schwartz et al. | |
| 2006/0247702 A1 | 11/2006 | Stegemann et al. | |
| 2007/0083243 A1 | 4/2007 | Prakash et al. | |
| 2007/0299475 A1 | 12/2007 | Levin et al. | |
| 2008/0077187 A1 | 3/2008 | Levin et al. | |
| 2008/0109043 A1 | 5/2008 | Salo et al. | |
| 2009/0018608 A1 | 1/2009 | Schwartz et al. | |
| 2009/0036940 A1 | 2/2009 | Wei et al. | |
| 2009/0069859 A1 | 3/2009 | Whinnett et al. | |
| 2009/0082823 A1 | 3/2009 | Shuros et al. | |
| 2009/0207028 A1 | 8/2009 | Kubey et al. | |
| 2009/0240298 A1 | 9/2009 | Lian et al. | |
| 2009/0247893 A1 | 10/2009 | Lapinlampi et al. | |
| 2009/0254141 A1 | 10/2009 | Kramer et al. | |
| 2009/0281440 A1 | 11/2009 | Farazi et al. | |
| 2009/0281591 A1 | 11/2009 | Shuros et al. | |
| 2009/0318995 A1 | 12/2009 | Keel et al. | |
| 2010/0069989 A1 | 3/2010 | Shipley et al. | |
| 2010/0087889 A1 | 4/2010 | Maskara et al. | |
| 2010/0094370 A1 | 4/2010 | Levin et al. | |
| 2010/0121397 A1 | 5/2010 | Cholette | |
| 2010/0121402 A1 | 5/2010 | Arcot-Krishnamurthy et al. | |

FOREIGN PATENT DOCUMENTS

| | | |
|---|---|---|
| WO | WO 03/000252 | 1/2003 |
| WO | 2007021258 | 2/2007 |

OTHER PUBLICATIONS

Angelo Auricchio et al., "Effect of Pacing Chamber and Atrioventricular Delay on Acute Systolic Function of Paced Patients With Congestive Heart Failure", Circulation (Journal of the American Heart Association), Jun. 15, 1999, pp. 2993-3001, vol. 23, Published by the American Heart Association, Dallas, TX.

Angelo Auricchio et al., "Cardiac Resynchronization Therapy Restores Optimal Atrioventricular Mechanical Timing in Heart Failure Patients With Ventricular Conduction Delay", Journal of the American College of Cardiology, Apr. 3, 2002, pp. 1163-1169, vol. 39, No. 7, Published by Elsevier Science Inc.

Walter F. Kerwin et al., "Ventricular Contraction Abnormalities in Dilated Cardiomyopathy: Effect of Biventricular Pacing to Correct Interventricular Dyssynchrony", Journal of the American College of Cardiology, Apr. 2000, pp. 1221-1227, vol. 35, No. 5, Published by Elsevier Science Inc.

Lili Liu et al., "Left ventricular resynchronization therapy in a canine model of left bundle branch block", American Journal of Physiology—Heart and Circulatory Physiology, Jun. 2002, pp. H2238-H2244, vol. 282.

Brendan O'Cochlain et al., "The Effect of Variation in the Interval Between Right and Left Ventricular Activation on Paced QRS Duration", Journal of Pacing Clinical Electrophysiology, Dec. 2001, pp. 1780-1782, vol. 24, No. 12, Published by Futura Publishing Company, Inc., Armonk, NY.

C. Pappone et al., "Cardiac pacing in heart failure patients with left bundle branch block: impact of pacing site for optimizing left ventricular resynchronization", Ital Heart J, Jul. 2000, pp. 464-469, vol. 1.

Giovanni B. Perego et al., "*Simultaneous* vs. *sequential biventricular pacing in dilated cardiomyopathy*: an acute hemodynamic study", The European Journal of Heart Failure, 2003, pp. 305-313, vol. 5, Published by Elsevier Science Inc.

Xander A. A. M. Verbeek et al., "Quantification of interventricular asynchrony during LBBB and ventricular pacing", American Journal of Physiology—Heart and Circulatory Physiology, Oct. 2002, pp. H1370-H1378, vol. 283.

Xander A. A. M. Verbeek et al., "Intra-Ventricular Resynchronization for Optimal Left Ventricular Function During Pacing in Experimental Left Bundle Branch Block", Journal of the American College of Cardiology, Aug. 6, 2003, pp. 558-567, vol. 42, No. 3, Published by Elsevier Science Inc.

PCT Notification of Transmittal of the International Search Report and the Written Opinion of the International Searching Authority, or the Declaration, International Application No. PCT/US05/28415, from the International Searching Authority dated Jan. 19, 2006.

PCT Notification Concerning Transmittal of Copy of International Preliminary Report on Patentability (IPER), International Application No. PCT/US2005/028415, from the International Bureau dated Feb. 21, 2008.

\* cited by examiner

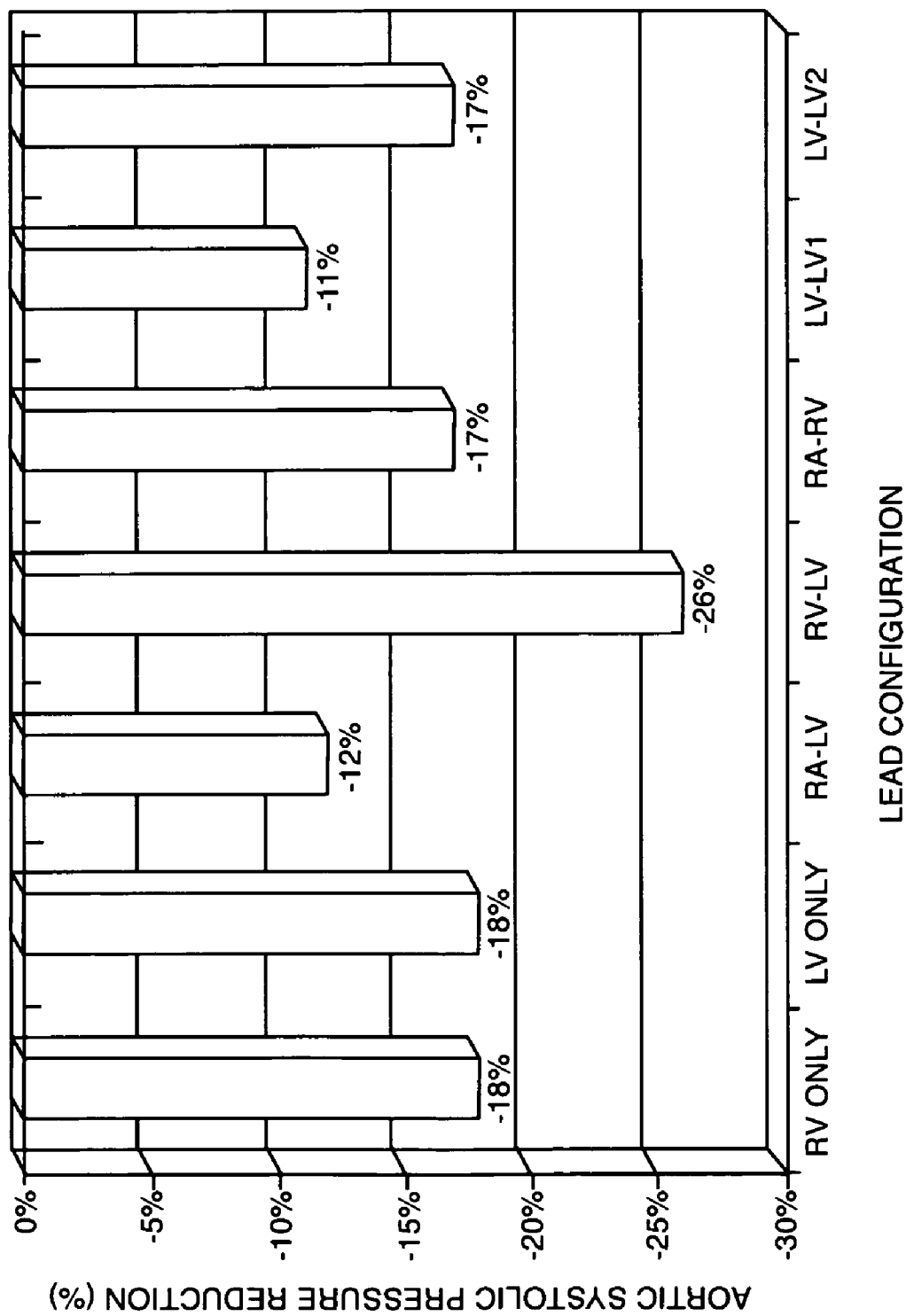

CARDIAC STIMULATION APPARATUS AND METHOD FOR THE CONTROL OF HYPERTENSION

CROSS REFERENCE TO RELATED CASES

The present case is a continuation in part application of U.S. Utility application Ser. No. 11/057,279; filed Feb. 11, 2005, now abandoned, which is the utility conversion of U.S. Provisional Application 60/544,112 filed Feb. 12, 2004 entitled "Antihypertensive Cardiac Pacing" which is incorporated herein in its entirety. Applicant claims the benefit of the earlier filing date of the parent application and the provisional application for all that they contain and teach.

FIELD OF THE INVENTION

The present invention relates generally to electrical stimulation of the heart, and more particularly to stimulating the heart at times and locations to control the patient's blood pressure as a treatment for hypertension.

BACKGROUND OF THE INVENTION

Electrical stimulation of cardiac tissue as a therapy has been known and practiced since the 1960s. By 1967 pacemakers set a minimum heart rate and intervened to stimulate or pace the right ventricle of the heart at a fixed rate if the natural heart rate dropped below this minimum heart rate floor (VVI or "demand" pacing). This treatment, originally prescribed for a slow heart rate or rhythm (bradycardia), was improved with the advent multiple chamber devices. These so-called "dual chamber" pacing devices track the prevailing heart rate and rhythm, and intervene to treat the heart with more physiologic pacing mode (VAT, DVI, DDD). Such devices are well suited to patients with intermittent rhythm disturbances. As a group, these well known pacing modalities allow a more natural heart rate and rhythm to predominate over a wide range of conditions.

Other heart rhythm diseases have also been treated with more specialized devices that interact with the heart to control too-fast rhythms (tachycardia) of several differing etiologies. Antitachyardia therapeutic devices may pace the heart rapidly to interrupt potentially lethal arrhythmias. Implantable Cardioverter Defibrillators (ICD) with multiple leads and several stimulus power levels have been used to treat the lethal arrhythmias such as ventricular fibrillation, while lower power, multiple site pacing may aid patients in heart failure (bi-ventricular pacing) by re-synchronizing the right and left ventricles.

Throughout the history of pacing it has been observed that the act of stimulating the heart can have a direct and substantial impact on the blood pressure of the patient. Since the earliest days, it has been noted that ventricular pacing (VVI) may result in decreased cardiac output that is often associated with low blood pressure, resulting in a condition called "Pacemaker Syndrome". Although this term is generic to a range of mechanisms and pacemaker interactions, it is a widely held belief that some of the impetus for development of dual chamber pacing modalities derived from the effort to alleviate the pacemaker syndrome that was observed to be concomitant with the wide scale adoption of single chamber pacemakers.

It should also be noted that more recently some implanted stimulation devices have been proposed to "pace" or electrically stimulate the carotid sinus baroreceptors of a patient to control blood pressure as a way to treat hypertension.

Other device based approaches for reducing blood pressure through pacing are known. For example, device based therapies include pacemaker type stimulators for non-cardiac structures for treating hypertension as taught by U.S. Pat. No. 6,073,048 to Kieval which discloses a device that delivers stimulation to arterial baroreceptors to lower systemic blood pressure indirectly through neurogenically mediated pathways.

Pacemakers that incorporate pressure sensors are known from U.S. Pat. No. 6,522,926 to Kieval which shows a pacemaker for optimizing the AV delay interval of a patient's heart to increase cardiac output.

SUMMARY OF THE INVENTION

In contrast to the prior art in which electrical stimulation acts principally to speed up or slow down the heart rate or its rhythm, this invention modifies observed blood pressure using electrical stimulation of the heart. The methodology may be carried out with a dedicated device standing alone or it may be incorporated into a conventional pacemaker that carries out recognized and known pacing therapies. In this latter instance the methodology and device would be a feature integrated into the composite pacemaker. It is expected that in most implementations the device will be fully implanted, battery powered, and automatic in its operation. In this disclosure the device and antihypertensive stimulation protocol is disclosed in the context of an implanted dual chamber pacemaker providing anti-bradycardia therapy.

In the preferred embodiment, the stimulation is electrical, but the stimulation source could be from a variety of sources, including, but not limited to mechanical, ultrasound, laser, vibration and microwave. In some embodiments, a pressure transducer signal is used to invoke the antihypertensive therapeutic stimulation and the therapy occurs episodically. In other embodiments blood pressure measurement may be used to adjust the parameters of the anti-hypertensive stimulation therapy to arrive at an anti-hypertensive appropriate dose for the patient. The pressure transducer may be inside the patient, in the "can" or on a lead or catheter. Alternatively, the pressure transducer may be outside the patient and communicate with an implanted device that carries out the therapy, or may simply be read by the patient or clinician to adjust the operating parameters of the implanted device to arrive at the desired blood pressure level. In the simplest embodiment the pressure measurement may be made with a conventional pressure cuff, and adjustments to the implanted device accomplished manually in a manner that is analogous to the adjustment of the dose of an anti-hypertensive medication. In one embodiment of the present disclosure the pressure transducer is placed across the interventricular septum to measure the pressure in the left ventricle. In another embodiment the pressure measurement is made by a pressure capsule on a lead or catheter in the right heart. In a further embodiment the pressure measurement is made externally to the body. In yet another embodiment a sensor may be placed in an artery for pressure measurement.

The antihypertensive therapy can take place while the patient is in normal sinus rhythm or the therapy may occur within a paced rhythm. In many embodiments the stimulation regime will take place in the right heart at times that are early compared to the native cardiac rhythm or to the timing of an underlying anti-bradycardia pacing therapy. The stimulation delivered to heart tissue is preferably above the capture threshold of the heart tissue but may be above, or below the capture threshold of the cardiac tissue at the stimulation site. The stimulation site and pulse generator may also be used to deliver conventional anti-bradycardia pacing therapy. Other nontraditional stimulation sites may be selected and may be preferable to carry out the anti-hypertensive stimulation therapy.

While several mechanisms may be involved in the beneficial modulation of the blood pressure by the anti-hypertensive stimulation therapy, in one embodiment electrical energy may be applied to the right heart at times and locations that result in diminished stroke volume accompanied by an increase in rate to sustain cardiac output (decreasing left ventricular filling pressure/volume); or stimulation may be applied to the septum or left heart to reduce cardiac contractility thereby resulting in a prolonged ejection of left ventricular blood volume and reduced peak blood pressure.

It is understood that the heart exhibits several interrelated compensatory control mechanisms and it is expected that intermittent application of the antihypertensive stimulation therapy will provide the best results for the patient. For example, anti-hypertensive therapy may be applied for one or more beats, followed by intrinsic (or anti-bradycardia paced) beats. If additional blood pressure reduction is desired, parameters in the implanted device may be adjusted such that the number of anti-hypertensive beats is increased, or the number of intrinsic beats is decreased.

BRIEF DESCRIPTION OF THE DRAWINGS

In the several figures of the drawing identical reference numerals indicate identical structure wherein:

FIG. 9 there is no FIG. 9;

FIG. 10 there is no FIG. 10;

DETAILED DESCRIPTION OF THE INVENTION

Cardiac Mechanics Background

If ventricular blood pressure (P) is plotted against volume (V) for the right or left ventricles a representative pressure volume (PV) loop is generated. The area bounded by the loop reflects the amount of mechanical work done by the heart pumping blood during that beat. Cardiac events occur in sequence, and these correspond to various locations around the loop. Time proceeds counterclockwise around the loop and if beats were identical all loop points and time events would overly one on another on the 2-D figure. PV loops for sequential beats form overlapping trajectories on the figure.

Figure 2:
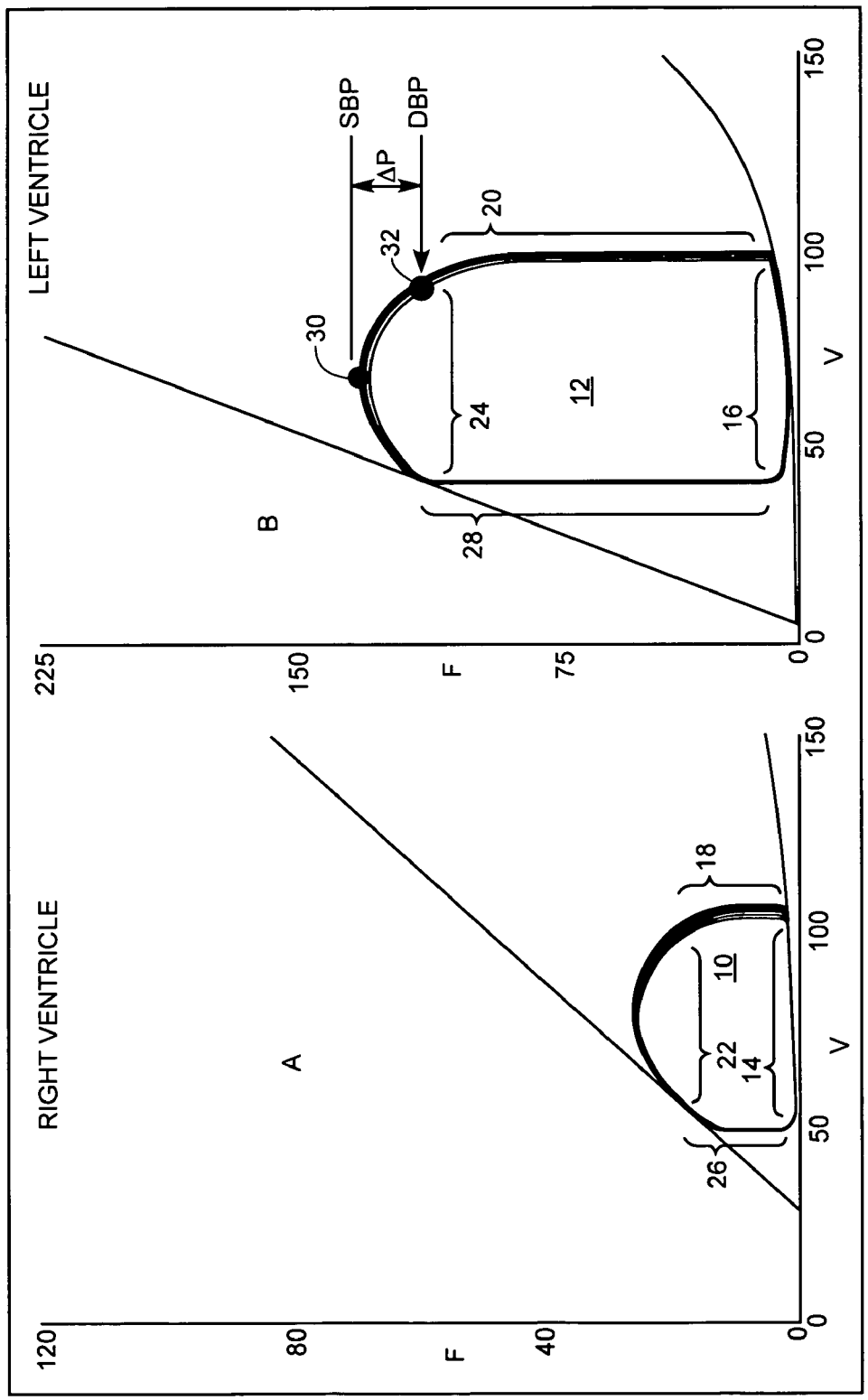
FIG. 2 is divided into two panels showing the action of the normal healthy heart during a normal sinus beat.

FIG. 2 represents the activity of a normal healthy heart presented in the "PV Loop paradigm", for this reason it is labeled "prior art". In the figure a separate PV loop for each "side" of the heart is shown separately. The right heart is shown in panel A where the PV loop 10 of the right ventricle is seen. The left heart is depicted in panel B which shows the PV loop 12 of the right ventricle.

Both ventricles fill easily as depicted by the lower segment 14 of the RV PV loop and the lower segment of the LV PV loop 16. Note that these figures show relatively little change in pressure as the ventricles fill during diastole. In this induction segment the cardiac muscles are "relaxed". From the electrographic viewpoint this filling occurs during the last part of the inter-complex interval. After activation via the sinoatrial (SA) node and the conduction system of the heart, the muscles of the ventricles contract quickly raising the pressure without much change in volume. The isovolumic (constant ventricular volume) contraction is seen in sections 18 and 20 respectively in panel A and B reflect this systolic phase of the heartbeat which corresponds to the electrographic QRS complex. After a time of isovolumic contraction the heart valves open and the ejection phase begins. The ejection phase segments 22 and 24 respectively correspond to this phase of the heartbeat. Each PV loop of the heart is completed by the isovolumic relaxation phase of the cycle shown as segment 26 and 28 respectively in panel A and B.

The pulsatile pumps of the right and left heart must pump the same amount of blood on average. They are coupled by a complex network of the lungs and vascular system which are somewhat elastic, so that pressure damping occurs in this system. The pressure and flow at the level of the capillaries is nearly steady state while pressure differences in the major arterial vessels are easily detected as the familiar ratio of systolic blood pressure (SBP) 30 to diastolic blood pressure (DBP) 32. In general a less compliant vascular network will increase the afterload on the ventricle and the work of the ventricle is evidenced as high blood pressure at lower flow. The healthy patient, for the same ventricular work, will show more blood flow and lower peak blood pressures.

Figure 1:
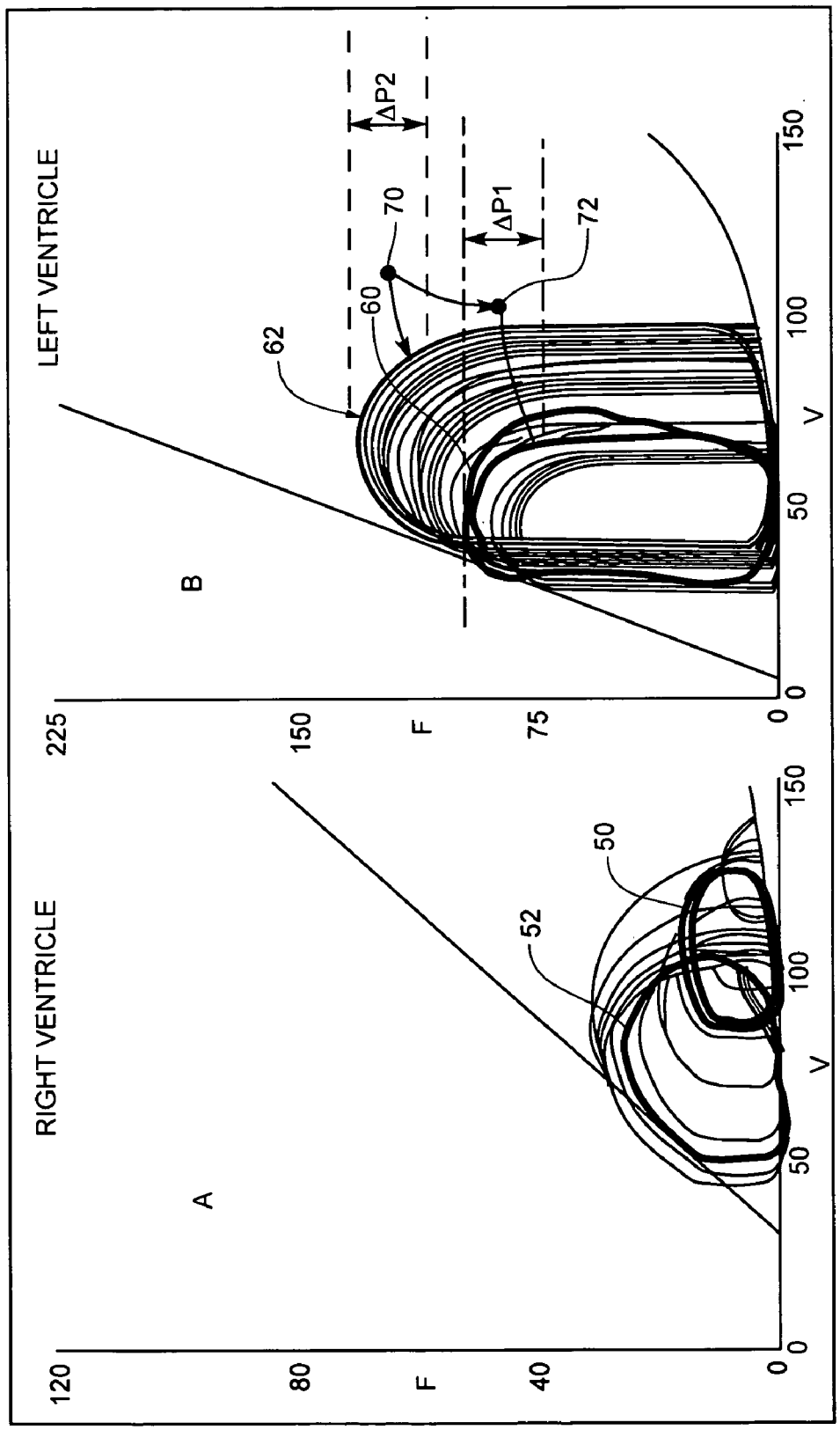
FIG. 1 is divided into two panels showing the action of the right heart and left heart during the antihypertensive therapy.

FIG. 1 shows an implementation of the invention where a anti-hypertension stimulation intervention is provided to the right heart. The application of the anti-hypertension stimulation causes the Right ventricle to exhibit a characteristic PV loop 50. This occurs within a heart where the nominal PV loop without the stimulation is of the form seen as PV loop 52. The unmarked trajectories depict transition PV loops from one form to another in response to anti-hypertensive stimulation. By altering the contractility of the right ventricle the resultant PV loop on the ventricular side moves from PV loop 62 to 60. The peak LV SBP (peak LV Pressure) has been reduced. The PV loops will follow the unmarked trajectories in the figure from one loop to another because of the compliance of the vascular system and the intervention of compensatory mechanisms. The stimulation process is invoked in this implementation by detection of blood pressure above a threshold. The threshold is depicted in the diagram as point 70 on which corresponds to a detected trigger pressure. There are many alternative techniques for declaring a pressure threshold based intervention however, it is expected that a number of consecutive beats with a measured pressure (after valve opening) that exceeds a threshold invokes the stimulation regime set forth in FIG. 6 or FIG. 7 or FIG. 8 The goal of the therapy is to move the measured blood pressure (BP) to point 72 in a number of beats. It is expected that the system will operate open loop that is the therapy is invoked when a threshold is reached and the therapy occurs over a fixed time or fixed number of beats.

Figure 3:
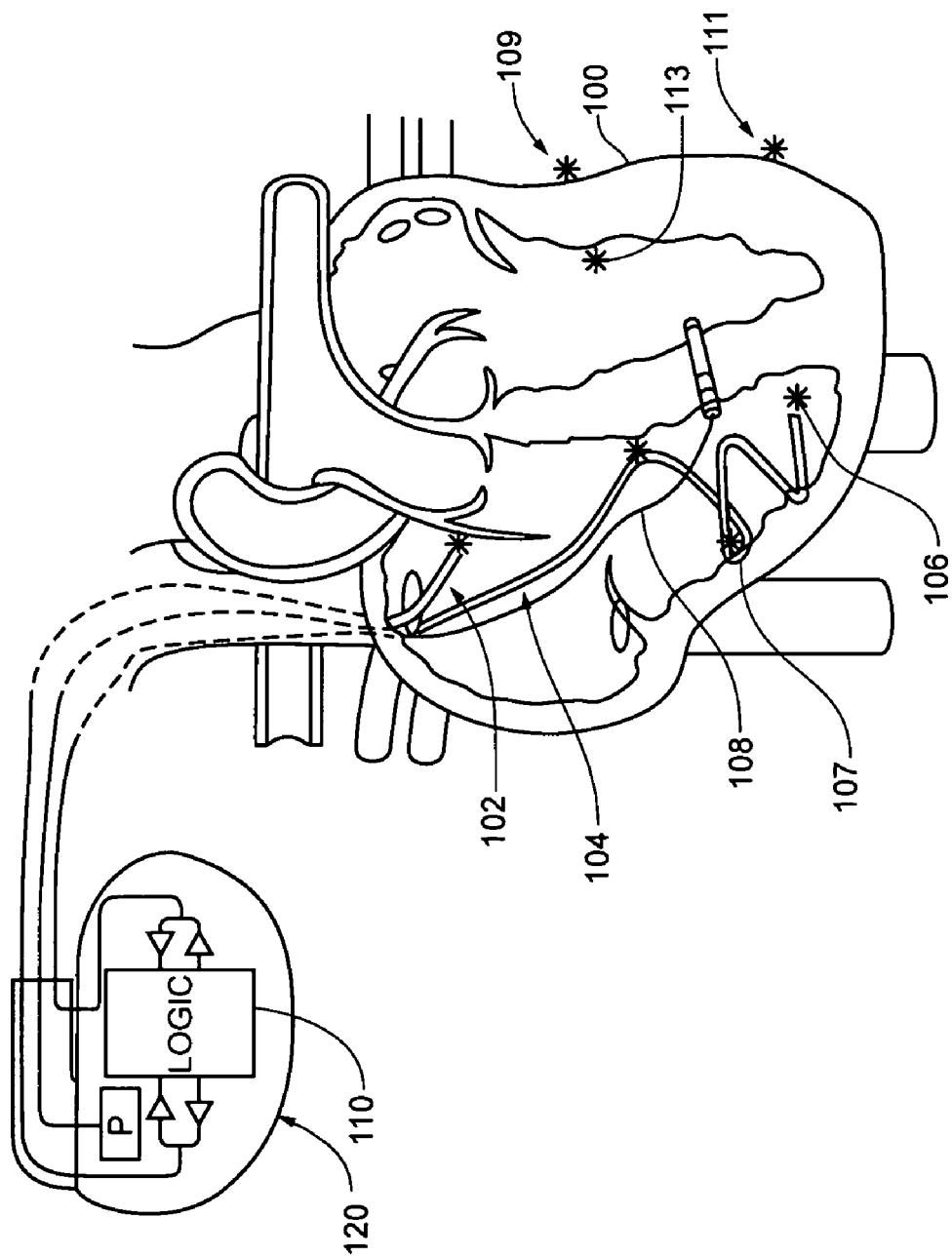
FIG. 3 is schematic diagram of the components of a representative device for carrying out the therapy.
Figure 4:
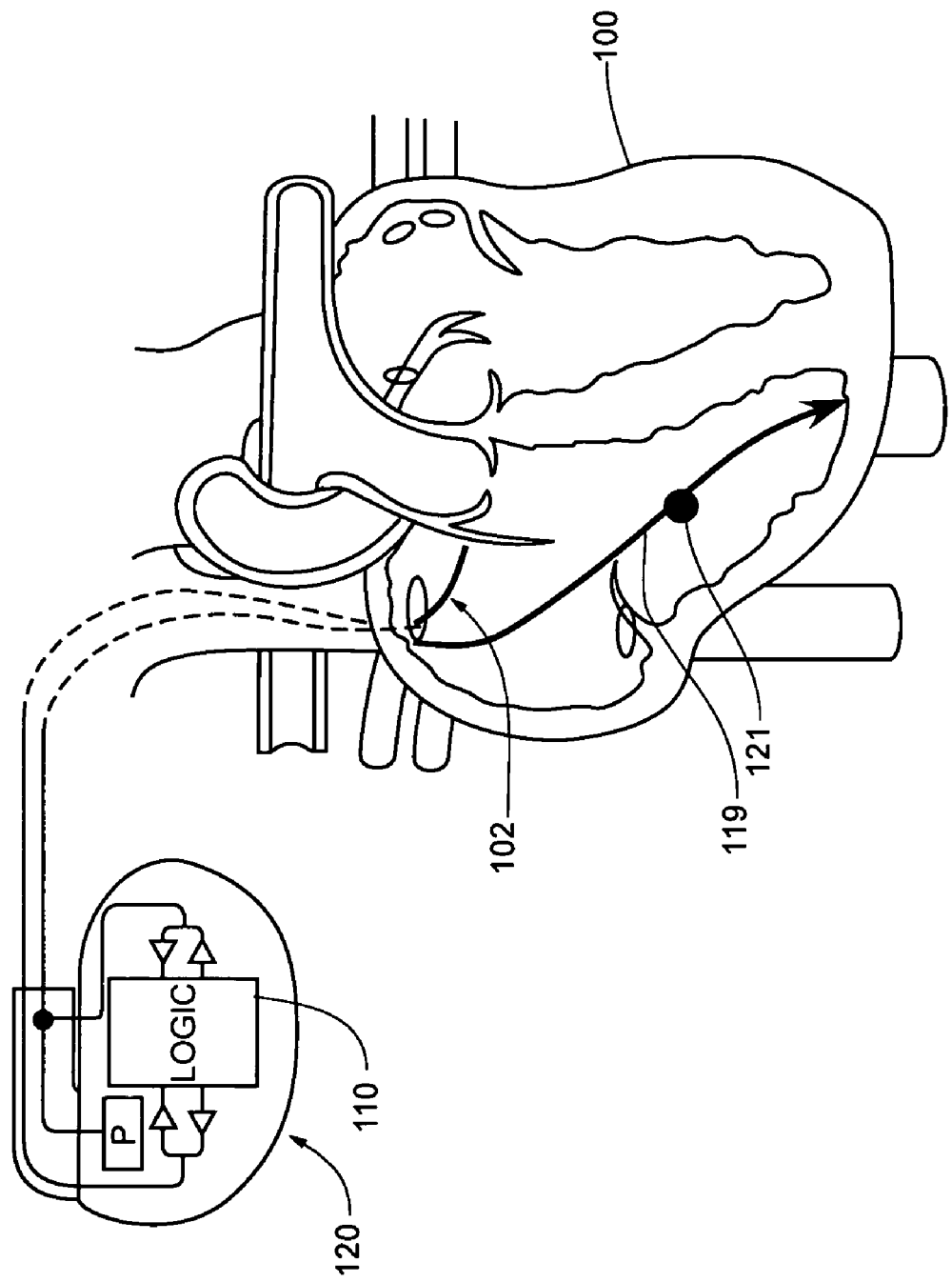
FIG. 4 is a schematic diagram of the components of a representative device for carrying out the therapy.

FIG. 3 is a highly schematic diagram that corresponds to the proposed hardware device configuration. The patient's heart 100 has several lead systems implanted. An arterial catheter 102 places a stimulation electrode in the right atrium. On the ventricular side several leads are proposed. For example a separate transeptal pressure sensing catheter is shown as catheter 108. A right ventricular lead 104 is shown with a proximal stimulation electrode 107 and a distal stimulation electrode 106. Additional stimulation locations on the left heart may be provided via separate leads (not shown for clarity) to intrapericardial sites 109 and 111. It is also possible to reach the interior of the left heart and a lead on the endocardial wall at site 113 may be useful in carrying out the invention. These catheters are coupled to a remote electrical stimulation device 120 that is placed in the patient's chest and attached to the catheters through the cardiovascular system. This set of stimulation catheters is sufficient to carry out traditional dual chamber stimulation modalities and may be likewise used to provide stimulation regimes for carrying out the present invention. In the device 120 logic 110 sets several escape intervals to control conventional pacing. This technology is well known and no detailed description is needed to carry out the invention. The invention is disclosed in connection with a dual chamber DDD mode device were an atrial escape interval is defined to set a lower atrial pacing rate. A ventricular escape interval is also timed by logic 110. Although the transeptal pressure transducer has the advantage of directly measuring left ventricular pressure, other pressure sending methodologies may be adopted. FIG. 4 shows a pressure sensing capsule along the length of the ventricular catheter 119. The capsule 121 reports right ventricular pressure to the logic 110 in the device and adjustments will need be made to the threshold to initiate therapy.

Figure 5:
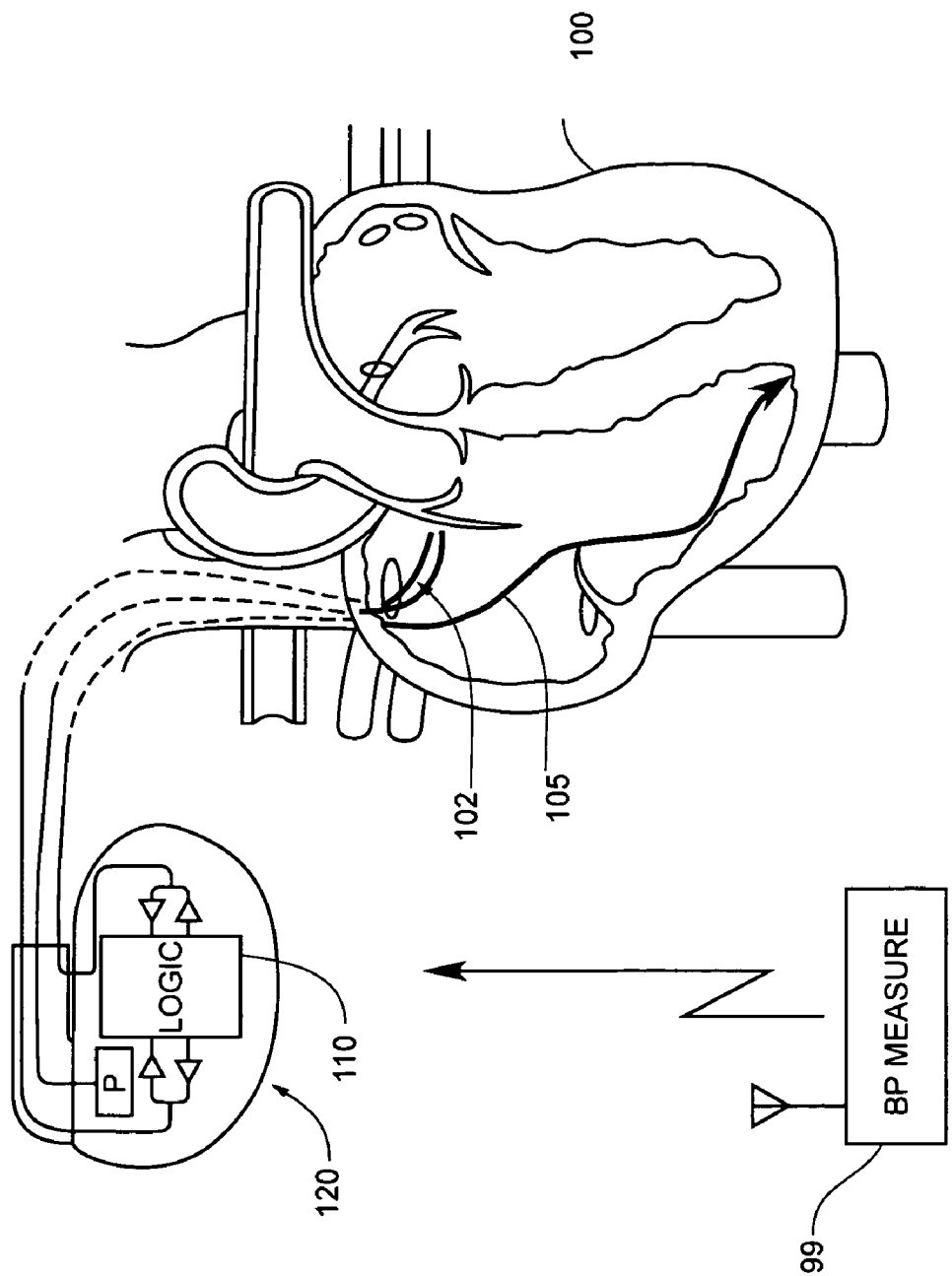
FIG. 5 is a schematic diagram of the components of a representative device for carrying out the therapy.

FIG. 5 shows an external blood pressure sensor that may be a conventional sphygmomanometer cuff device. The external sensor 99 telemeters the blood pressure data that is used to initial the therapy to the implanted device. Periodically blood pressure may be measured to truncate, stop or otherwise modify the therapy. In one embodiment, the patient's blood pressure is measured by the clinician, and the parameters of the anti-hypertension stimulation are modified by the clinician to achieve the target blood pressure In operation the transeptal pressure measurement device will provide information regarding the pressure in the ventricle and most particularly pressure in the ventricle corresponding to the time period associated with the minimum and maximum pressure after the heart valves open during the ejection period. If the measured pressure exceeds a trigger value over a long enough period of time the stimulation is commanded to insert an additional antihypertensive stimulation therapy to drive the measured pressure to a lower value.

For example, turning to FIG. 1, if there is a pressure within the range delta P2 (see item 70 FIG. 1) the device may invoke a therapy attempting to drive the measured pressure to the range delta P1 (see item 71 in FIG. 1). A successful treatment may be observed in the left ventricle as an average measured pressure moving from point 70 on loop 62 to point 72 on loop 60. In essence the stimulation regime moves the heart from a loop 62 to a loop 60 via successive heart beat cycles.

Figure 6:
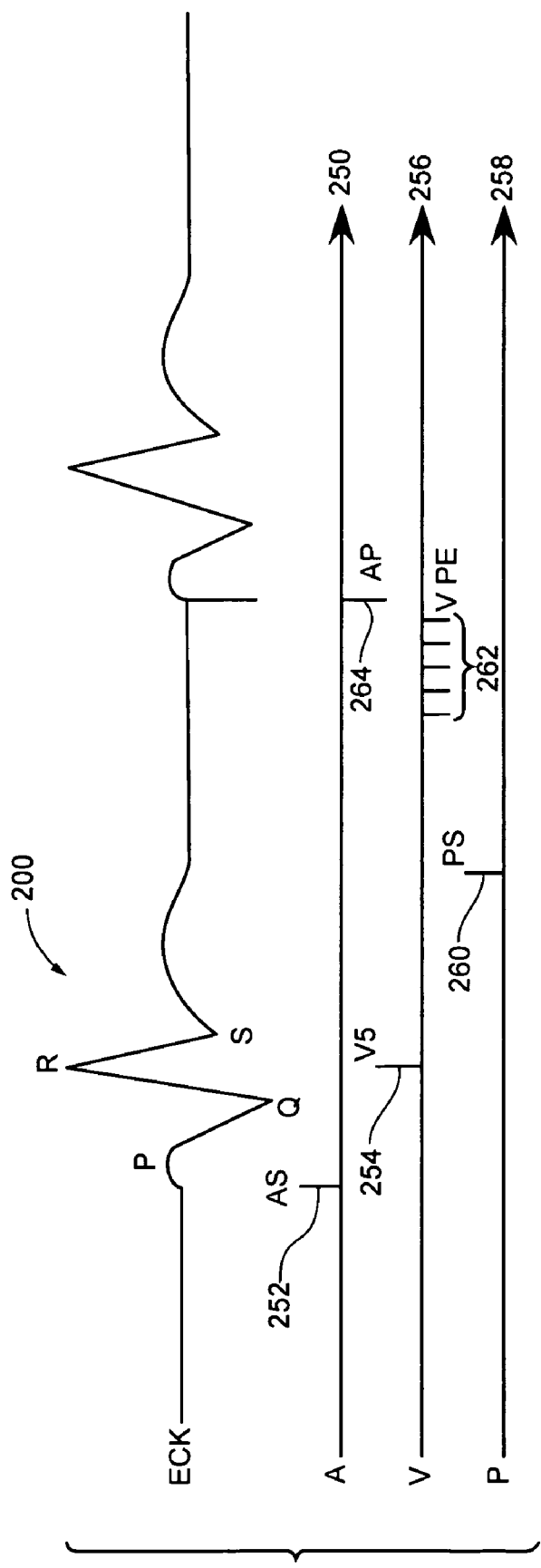
FIG. 6 is a timing diagram representative of an alternate method of carrying out the therapy; and, FIG. 7 is a timing diagram representative of an alternate method of carrying out the therapy.

There are a number of techniques that can be used to alter the PV loop of the right ventricle moving it from loop 52 to a shape more nearly similar to shape 50 in FIG. 1 panel A. One preferred technique is shown in FIG. 6, where the delivery of a stimulation level of energy on atrial stimulation catheter 102 preceded by multiple sub-threshold stimulation at multiple sites in the right ventricle including on the right ventricular free wall, through a multiple electrode ventricular catheter 104. As a consequence of this stimulation regime it is expected that the atrial filling of the right ventricle will be reduced during the stimulated beat and one or more normal sinus beats that follow. It is expected that the contractility of the right ventricle will be reduced due to pre-excitation followed by stimulation to capture at least one beat of the heart. FIG. 6 shows the interaction and integration of the hypertensive treatment with a conventional DDD pacing stimulation regime. Turning to FIG. 6 a naturally conducted sinus beat complex is shown as complex 200 comprising P, Q R, S and T segments. The P-wave is detected by an atrial sense amplifier coupled to the RA catheter 102 (FIG. 3) as seen on the atrial channel 250 of FIG. 4 as indicated by sense event 252. The conducted beat (QRS complex) is sensed by the system as indicated by event 254 on ventricular sensing channel 256. In this particular patient the transeptal pressure transducer of pressure sensing catheter 108 detects an excursion of ventricular pressure sufficient to invoke the stimulation therapy as indicated by event 260 on pressure channel 258. This detected pressure event occurs within the atrial escape interval of the pacing modality selected and in response the device is provides a series of sub-threshold ventricular stimuli as indicated by the multiple complex 262 delivered to the multiple site right ventricular stimulation catheter 104. After this pre-excitation of the right ventricle a stimulus is provided to the atrium provoking a P-wave. This AP event is shown on the atrial channel as event 264 and in this instance it results in a conducted beat. The pre-excitation of the right ventricle results in and will be observed as a loss of contractility in the right ventricle resulting in a PV loop similar to that shown as loop 50 in FIG. 1.

Figure 7:
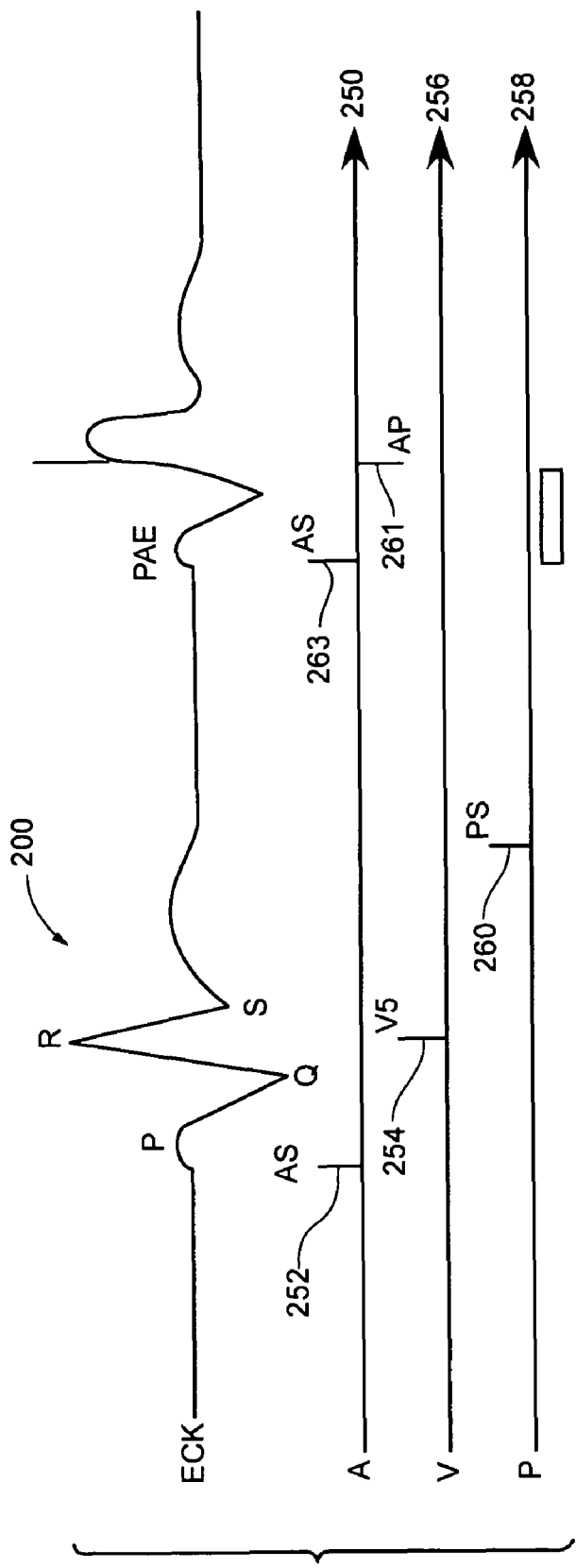

In FIG. 7 an alternate stimulation regime is shown for carrying out the invention. In this instance the detection of a pressure invoking event 260 is followed by atrial stimulation 261 after the next detected atrial depolarization 263. The "late" atrial depolarization 261 provoked by the pressure sensor results in a so-called fusion beat altering the left ventricular contraction and lowering the measured blood pressure form level 70 in FIG. 1 to level 72 in FIG. 1.

Figure 8:
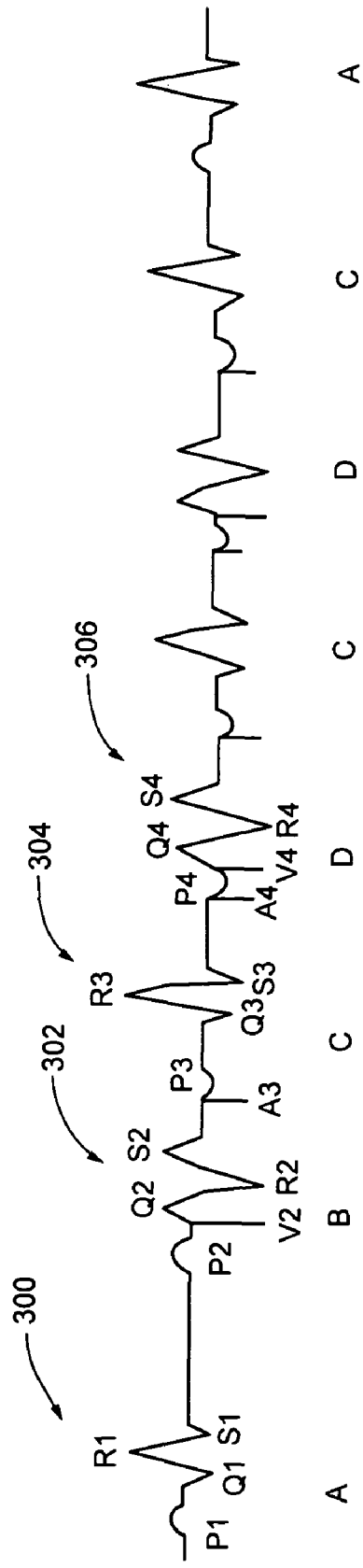
FIG. 8 is a timing diagram representative of an alternate method of carrying out the therapy.

In another embodiment, a right ventricular catheter is placed such that the electrode contacts the heart in the apex or on the free wall. A right atrial catheter is also used. A timing diagram of a representative stimulation sequence to achieve the anti-hypertensive therapy is shown in FIG. 8. An intrinsic heartbeat A is shown as 300 with a native PQR and S wave (the T wave is not shown to improve clarity). The normal heart interval is shown as the interval between atrial beats P1 and P2. The normal AV delay is shown as the interval between P1 and Q1. After the first heart beat 300 (Q1R1S1) shown, an intrinsic atrial contraction occurs at P2. The anti-hypertensive stimulation algorithm stimulates the ventricle early, after a short delay shown by P2 to V2. The stimulated ventricular beat 302 (Q2R2S2), being early, has lower blood flow and reduced blood pressure. For the next beat 304, the atrium is stimulated early, after a delay shown by P2 to A3. Stimulating the atrium early results in more heart beats per unit time to maintain cardiac output even though the individual heartbeats are each pumping less blood at lower blood pressure. A3 causes an atrial contraction P3, which is followed by a normal (unstimulated) AV delay shown by P3 to Q3. Heartbeat 304 (Q3R3S3) has reduced cardiac output and reduced blood pressure because the previous heartbeat (Q2R2S2) sent a diminished volume of blood to the lungs thus lowering left ventricular preload ("filling"). The next atrial event is stimulated at A4 followed by a stimulated ventricular beat 306 (Q4R4S4) after a short AV delay shown by the A4 to V4 delay. A pattern is evident from this concept. The first heartbeat was an intrinsic, or 'natural' beat (A), the second heartbeat was a transitional heart beat (B) having a normal interval but a shortened AV delay, the third heartbeat (C) had a shortened interval and a normal AV delay, and the fourth heartbeat (D) had a shortened interval and a shortened AV delay. An anti-hypertensive stimulation algorithm would count a certain number of A heartbeats, transition with a B heartbeat and then alternate for a programmed number of heartbeats alternating between C and D, ending with a C heartbeat before return to the A heartbeat. For example: AAAABCDCDCD-CAAAAB . . . etc. By decreasing the number of As and/or increasing the number of Cs and Ds the blood pressure reduction can be increased. Similarly, by decreasing the AV delay, the blood pressure can be further reduced (although the stimulated A to A interval would have to be increased to maintain cardiac output). The anti-hypertensive stimulation pattern described here is one possibility, and is not meant to limit the scope of the invention. It is also evident that any sequence can be generated that will create lowered blood pressure, that is, not all types of beats are essential for anti-hypertensive efficacy. The utility of the above sequences lie in preventing tachyphylaxis, and also not stimulating the heart with too many identical hypotensive beats in sequence that might lead to myopathic conditions. Some illustrative timing values follow. For a native heart rhythm having a P to P interval of 800 milliseconds, and an AV delay of 200 milliseconds, the stimulated A to A interval might be 700 milliseconds, and the stimulated AV delay might be 125 milliseconds. These values may be adjusted to increase or decrease the resulting blood pressure as desired, through effects on filling and muscle pump synchrony.

The parameters of the anti-hypertensive stimulation may be set by a clinician in a manner analogous to prescribing the dose of an anti-hypertension medication. Alternatively, an implanted blood pressure sensor may provide the input to a self-adjusting algorithm that automatically changes the parameters of the anti-hypertensive algorithm to achieve a target blood pressure level for the patient. A microprocessor based algorithm with device control may also be implemented to manage blood pressure reduction in real time.

Experimental Results

A single pig was paced at a variety of locations and under several parameters to provide a proof of concept for the invention. These results give rise to the FIGS. 11-21. To further clarify the invention certain definitions are adopted as follows.

DEFINITIONS

Some terms are not consistently used with precision in the medical literature. For this reason and for the purposes of interpreting this document the flowing definitions obtain:

Dyssynchrony is inducing a cardiac ejection cycle where the normal spatial contraction sequence is altered, either within a chamber or across multiple cardiac chambers. It may also refer to changes in contraction within a chamber or across multiple chambers in time. This means that the ejection of blood may for example be delayed, or prolonged.

Hypertension is defined as blood pressure systolic greater than 130 mmHg and/or diastolic greater than 90 mmHg.

Altered Contractility Profile is any disturbance of cardiac contraction that changes the power or energy of the heart. It is best measured by Emax from the end systolic pressure-volume loop relationship across multiple different loading conditions.

Pre Treatment Contractility Profile is the spatial and temporal contraction of individual and combined heart chambers prior to treatment. Contractility is best measured by Emax from the end systolic pressure-volume loop relationship across multiple different loading conditions.

Altered Ejection Profile is any disturbance of cardiac contraction, either within a chamber or across multiple chambers, that alters the resulting blood pressure as a bolus of blood is ejected from the heart.

Pre Treatment Ejection Profile is the spatial and temporal contraction of individual and combined heart chambers prior to treatment.

Congestive heart failure (CHF) is the name given to a spectrum of clinical symptoms. Usually the heart is enlarged and has an inability to sufficiently supply the body's blood pressure and flow needs without generating abnormal intra-cardiac blood pressures and/or flows.

Overview

In general terms, the inventive method is the intentional reduction of a patient's blood pressure though a cardiac stimulation regime that modifies the synchrony between or within the chambers of the heart. In the simplest embodiments which form illustrative but not limiting descriptions of the invention, pacing level stimuli are applied to the heart trough fixed leads of conventional design. The location of the leads or the timing of the stimuli is selected to alter the ejection profile or the contractility profile of that heartbeat. This modification or modulation of synchrony lowers blood pressure.

The preferred device is intended to deliver pacing level stimuli to the heart muscle to treat hypertension. In general the proposed and preferred device will monitor blood pressure with an indwelling blood pressure sensor and invoke a modulated synchrony therapy that results in blood pressure reduction. Experimental data and computer modeling verify that this therapy may be used alone or in conjunction with drug therapy.

A blood pressure (BP) transducer will be exposed to systolic, diastolic, and indeed continuous blood pressures and the device may compute a mean pressure for a beat or several beats of the heart. The BP data may also be used to compute dP/dt and other BP measures. In most examples the existence of hypertension is taken as a fixed BP threshold. However this threshold may vary as a function of time of day or measured activity. In essence the threshold used to invoke the therapy may itself vary.

The modified therapy may be invoked on demand in response to a BP threshold. Alternatively or in addition the therapy may be provided on a periodic (circadian) basis, or even on a beat-by-beat interval, for example skipping one or more beats. It may also be based on the coincidence of a threshold BP occurring simultaneously with measured activity. In some embodiments the therapy may be initiated by the patient or the physician on an acute basis. It is expected that the therapy will not be continuous, but it will be chronic, throughout the lifetime of a hypertensive patient.

Many drugs are traditionally used for hypertension. These include ACE inhibitors, Angiotensin Receptor blockers (ARB blockers), diuretics, beta receptor blockers, alpha receptor blockers, vasodilators, calcium channel blockers, centrally mediated antihypertensives such as methyl-DOPA, and others. The proposed therapy will enhance the antihypertensive effects of these drugs, allowing them to work more effectively. The therapy can be adjusted to modulate the hypertensive effects of these drugs.

In many hypertensive patients, blood pressure may be reduced by the administration of a drug that widens the QRS complex by dispersing the electrical-myocardial conduction and contraction that may be additive with the therapy. Candidate drugs include Tricyclic antidepressants, neuroleptics lithium procanimide lidocaine and derivatives, Class I antiarrhyythmics, salbutamol, flecainide, sertindole, propofenone, amiodarone and others.

Illustrative Embodiments and Associated Experiments

FIG. 11 through FIG. 17 are intended to show stimulation configurations that can be used to carry out or promote dyssynchrony between and within cardiac chambers to control blood pressure. Panel A of each figure shows the lead configuration and panel B shows the measured blood pressure reduction from a control measurement made in the same animal in normal sinus rhythm under otherwise similar conditions. Each panel of the data is taken at progressively higher pacing rates to capture the heart.

Thus in each instance the control for the experiment is taken in the same animal. The pre-treatment activation profile or prêt-treatment contractility profile corresponds to the BP in sinus rhythm. In a similar fashion the pre-treatment ejection profile corresponds to the BP in sinus rhythm.

Figure 11A:
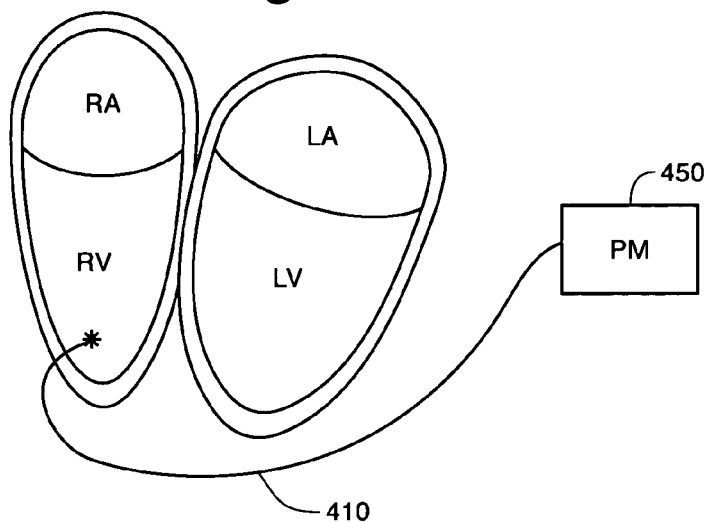
FIG. 11A is a VOO pacing configuration used in an experiment.
Figure 11B:
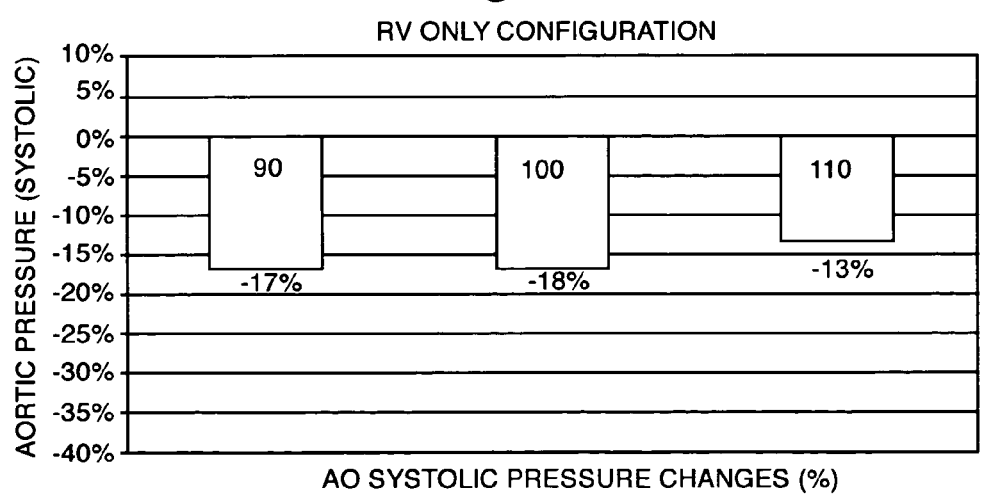
FIG. 11B is a data graph of blood pressure reduction at three pacing rates as measured in connection with an experiment.

FIG. 11A shows a lead 410 located in the apex of the RV coupled to a pacemaker 50 (PM). Capturing the heart at pacing rates of 90, 100, and 110 BPM results in the data shows in the graph of FIG. 1B. In this figure a reduction of BP by 16 percent is shown with no observable rate dependence.

Figure 12A:
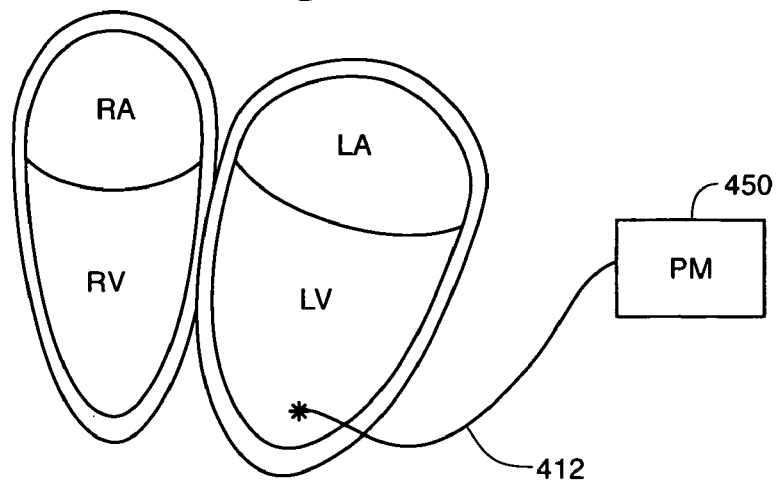
FIG. 12A is a VOO pacing configuration used in an experiment.
Figure 12B:
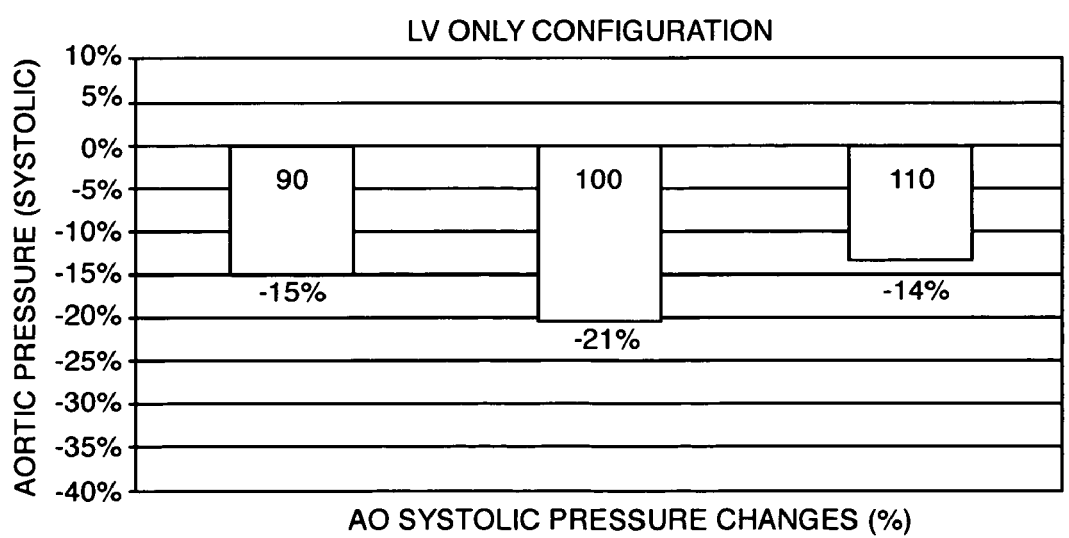
FIG. 12B is a data graph of blood pressure reduction at three pacing rates.

FIG. 2A shows a lead 412 located the apex of the LV with a VVI pacing configuration operating effectively in a VOO modality with pacemaker 450. The several pacing rates seen the graph of FIG. 12B show a −17% BP reduction without rate dependence.

Figure 13A:
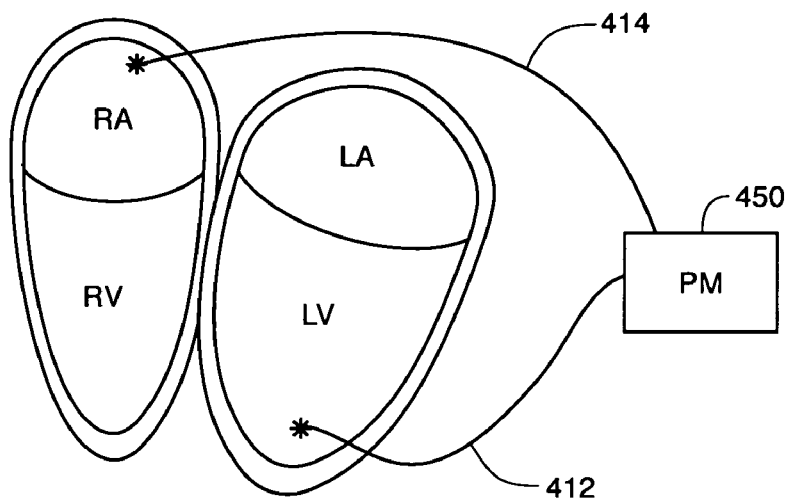
FIG. 13A is a DOO pacing configuration used in an experiment.
Figure 13B:
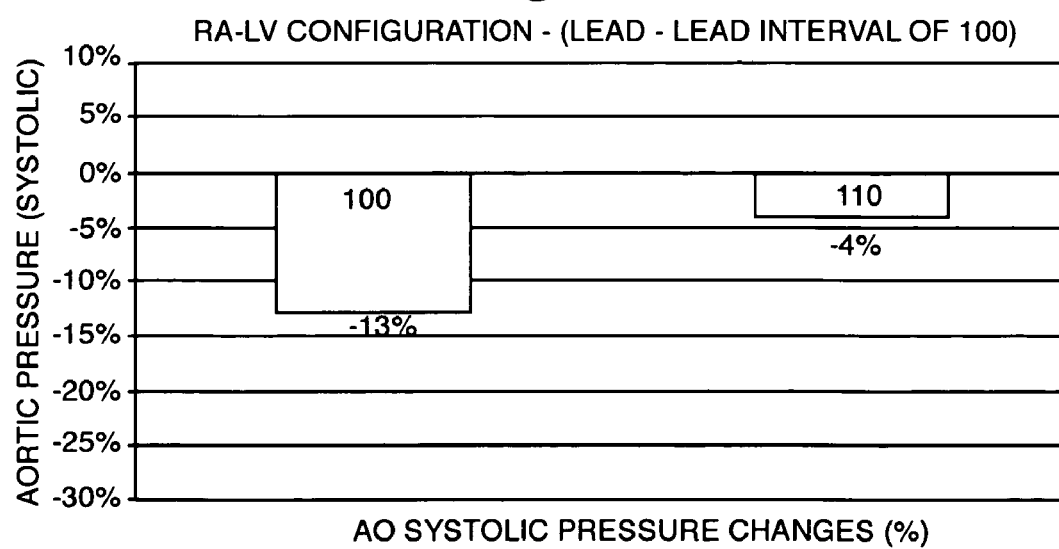
FIG. 13B is a data graph of blood pressure reduction at three pacing rates.

FIG. 13A shows a DOO modality where the right atrium is paced by lead 414 at a rate above sinus rhythm by pacemaker 450. The LV is paced through lead 412 after a variously short A-V delay preventing normal sinus conduction and contractility. FIG. 3B shows that a −8% BP reduction was achieved without observable dependence on the AV interval scan.

Figure 14A:
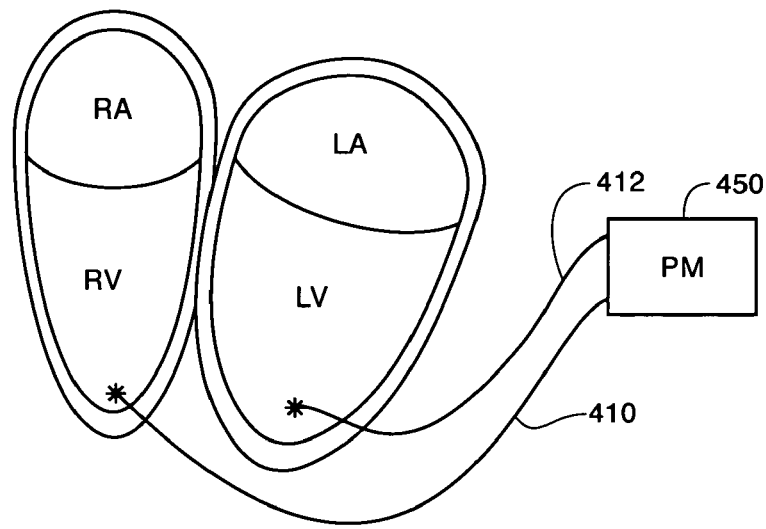
FIG. 14A is a biventricular DOO pacing configuration used in an experiment.
Figure 14B:
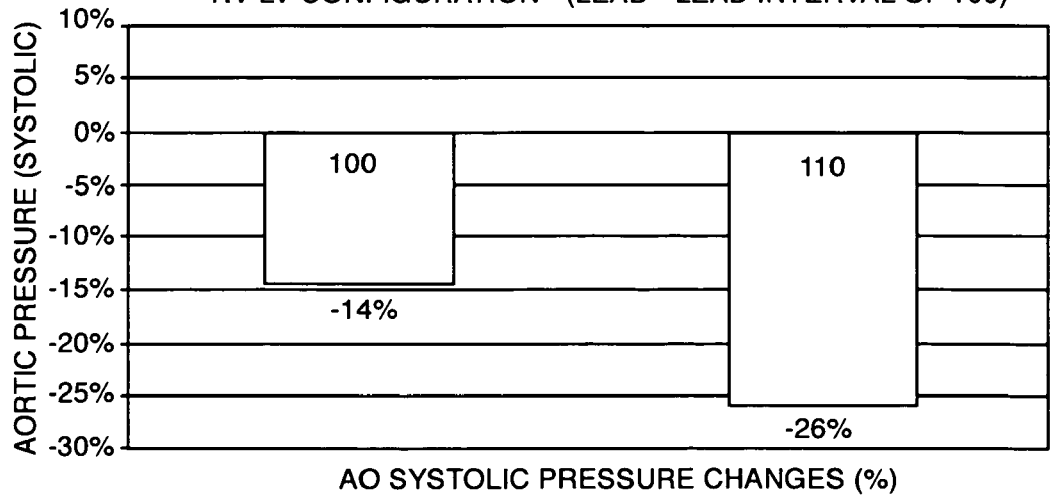
FIG. 14B is a data graph of blood pressure reduction at three pacing rates.

FIG. 14A shows a biventricular modality with VOO pacing of both the RV and the LV through leads 410 and 412. A progressive change was made to the RV-LV pacing interval. The RR interval was above sinus rhythm and scanned as well. No discernable dependence on rate was observed however a large −20% BP reduction was observed as seen in FIG. 14B.

Figure 15A:
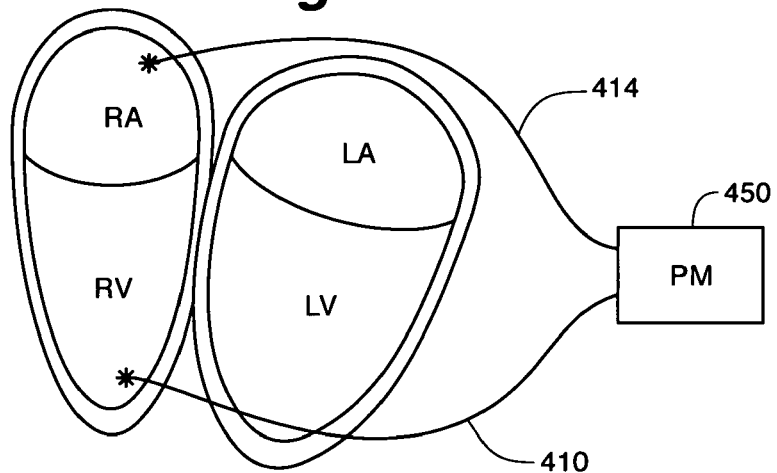
FIG. 15A is a DOO pacing configuration used in an experiment.
Figure 15B:
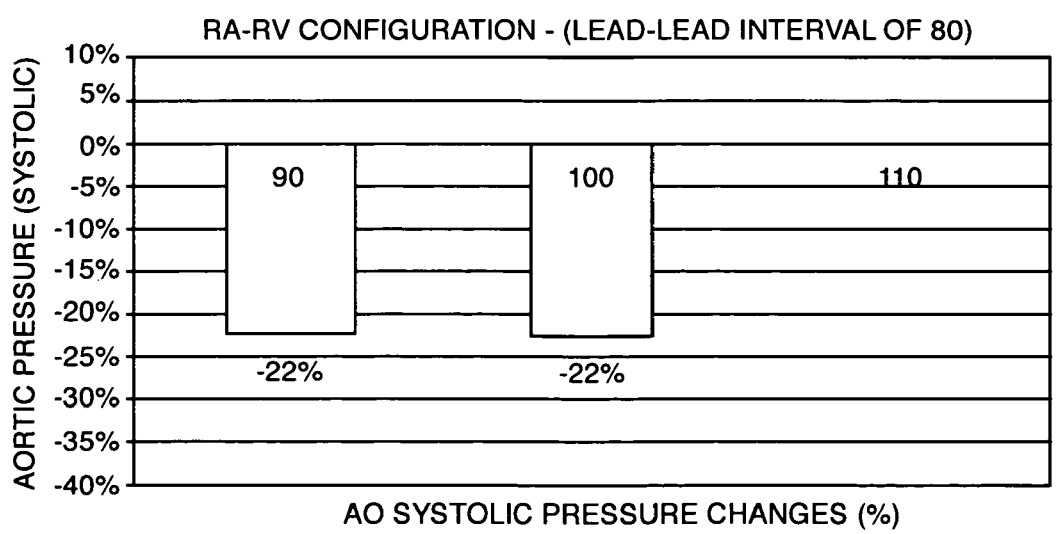
FIG. 15B is a data graph of blood pressure reduction at three pacing rates.

FIG. 15A shows a simple DOO pacing regime carried out in DDD mode. The AV delay was varied from 20 to 80 milliseconds and a marked reduction of BP −22% was observed as depicted in FIG. 15B.

Figure 16A:
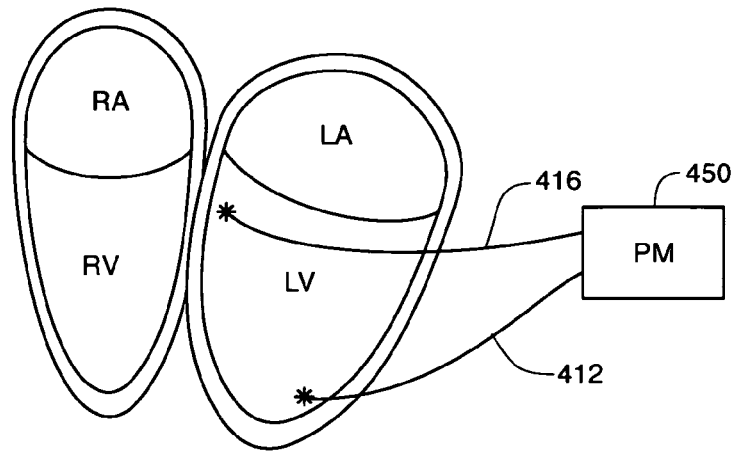
FIG. 16A is a multisite VOO pacing configuration used in an experiment.
Figure 16B:
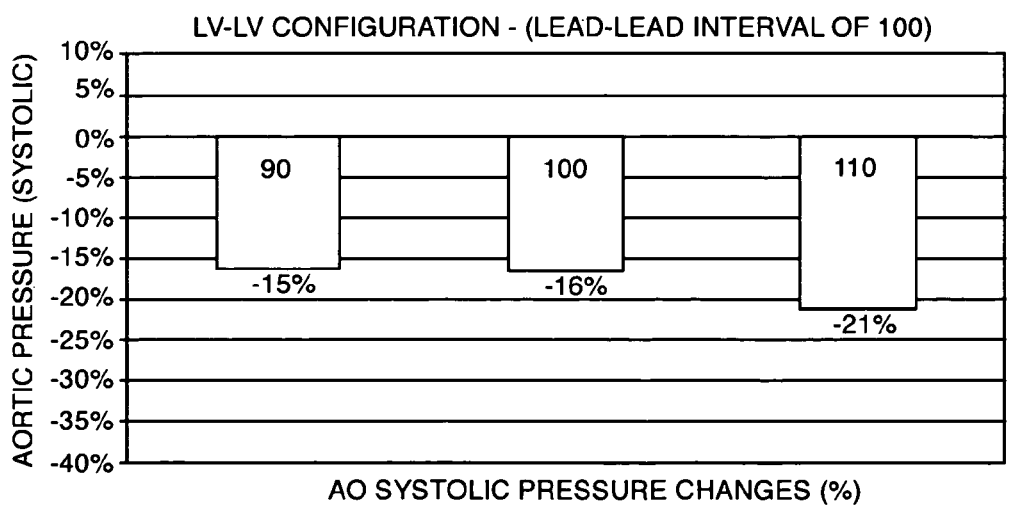
FIG. 16B is a data graph of blood pressure reduction at three pacing rates.

FIG. 16A shows a lead 410 in the LV at a first position and a second lead 412 located in the same chamber along the septum wall. The Lva–Lvb time interval was varied and FIG. 6B shows the −17% BP reduction achieved with this protocol.

Figure 17A:
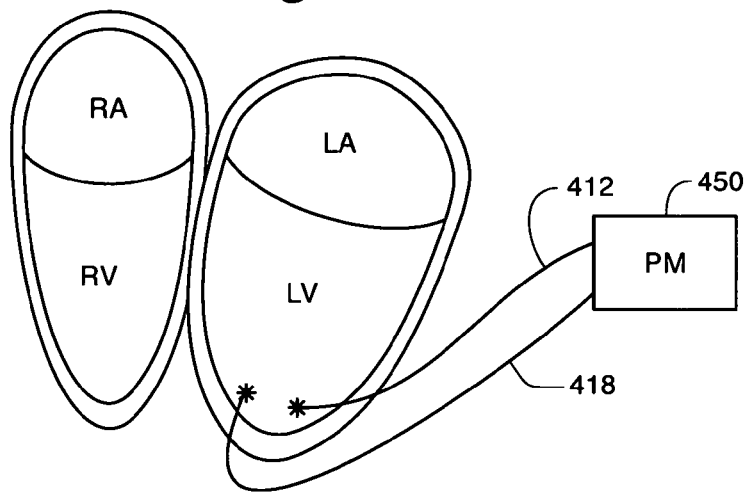
FIG. 17A is a multisite VOO pacing configuration used in an experiment.
Figure 17B:
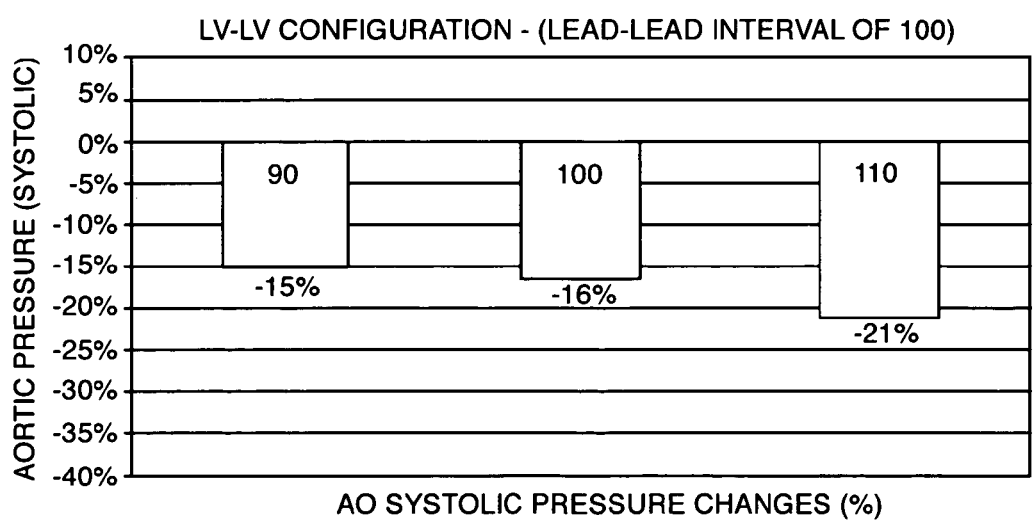
FIG. 17B is a data graph of blood pressure reduction at three pacing rates.

FIG. 17A shows an intraventricular anterior-inferior placement of leads 410 and 412. Burst pacing to 300 BPM showed a BP reduction of −10% as seen in FIG. 17B.

Figure 19:
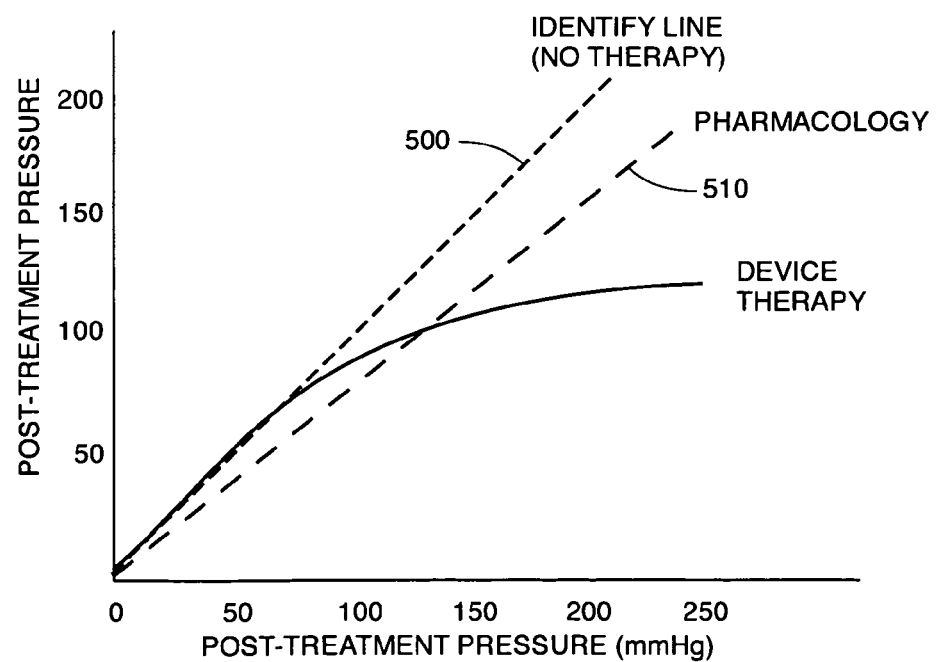
FIG. 19 is a diagram comparing drug therapy with the inventive therapy; and, FIG. 20 is a diagram showing how the inventive stimulation can be combined into a hybrid stimulator/drug therapy; and, FIG. 21 is a diagram summarizing pacing configurations.

FIG. 19 reflects additional computer modeling work was performed to evaluate the effect of modified synchrony pacing or stimulation protocols in comparison to a more conventional drug therapy.

FIG. 21 is a chart that summarizes the percent reduction based upon pacing configurations used in the experiment.

Figure 20:
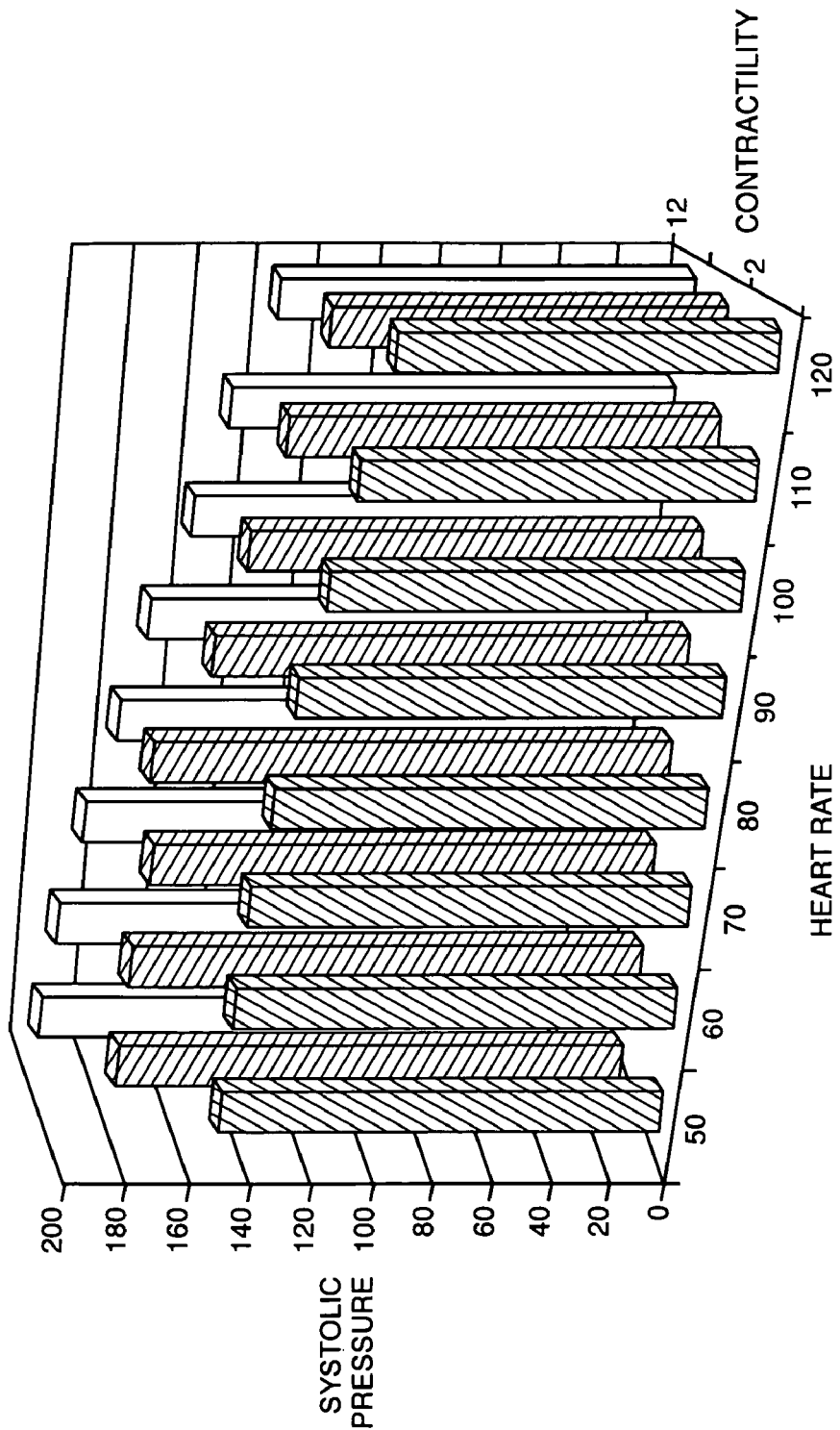

FIG. 20 reflects additional computer experimenting showing the value of a combined drug and stimulation therapy. In the figure at a lower than normal does of contractility reducing drug the percent change in BP reduction as a function of pacing increases dramatically. It is expected that combination therapy will be effective as well where the device therapy takes place in a patient with a "background" dose of the antihypertensive drug.

Interpretation and Benefits

FIG. 11 through FIG. 17 illustrate that any number of conventional stimulation regimes or therapies can be invoked to modify synchrony within or between the heart chambers. The best therapy may vary from patient to patient and some experimentation will be required to tailor a device for a patient. Based on the experiment it appears that the greatest reduction in BP is achieved with RV-LV dyssynchrony stimulation as seen in FIGS. 17A and 17B.

However it should be clear that the time the stimulus is delivered or the location of the stimulus can used to achieve the beneficial modification of synchrony independent of lead location.

FIG. 19 shows the relationship between the inventive cardiac stimulation and more traditional pharmacology on the control of blood pressure. Line 500 is the identity line corresponding to no therapy and the pre treatment and post treatment blood pressure is the "same". The pharmacology line 510 shows the control of blood pressure by a drug alone. For example, a patient having a pre treatment pressure of 200 mm of Hg is reduced to about 150 mm of Hg with a hypothetical drug. The linearity of the response however shows that the patient with an acceptable pretreatment BP of 100 mm of Hg would experience a drop to an undesirable BP of approximately 80 mm of Hg with the same drug. This treatment line shows that the systemic and chronic treatment of BP with drug can have an undesirable but concomitant effect on BP.

The device therapy is seen on line 420 which offers a BP reduction therapy which is modest and proportional to the need for therapy. The highly nonlinear behaviors of BP reduction with the inventive stimulation regime is of benefit to the patient since it brings a greater percent reduction benefit at the higher more pathologic BP values. Of considerable benefit is the fact the BP reduction occurs quickly with the onset of the stimulation regime and diminishes slowly when the stimulation is discontinued. It is preferred to have the therapy invoked when a threshold is exceeded and then continue for a fixed period of time for example 1 hour then the therapy stops. Activity monitors or real time clocks may be used as well.

Hardware Implementation

Figure 18:
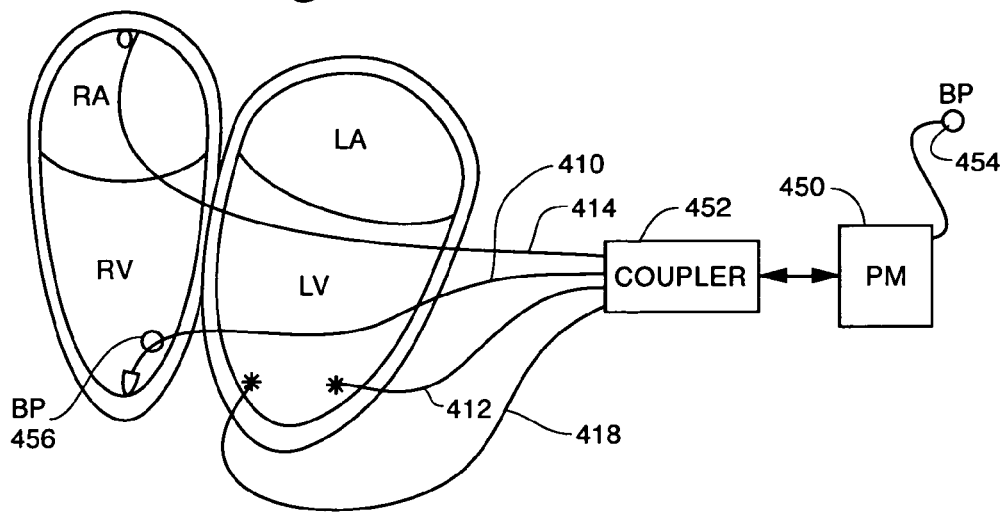
FIG. 18 is a diagram showing an exemplary and illustrative heart stimulator capable of carrying out the invention.

A representative but not limiting embodiment of a pacing device 150 to carry out the invention is shown in FIG. 18. The drawing shows a conventional heart stimulator capable of delivering heart stimulation to leads implanted at various locations in the heart. A connection block 452 allows selection of lead configurations as set forth in FIGS. 11 through 17. Typically only a subset of the leads shown in the figure are required for carrying out the therapy. Both sensing and pacing can occur at each lead location in the heart. All rates and timing intervals are available in the heart stimulator. A blood pressure sensor is located on a lead. Typical locations are in the RV or remotely in other regions of the vasculature. In another configuration, left ventricular cavity pressure can be measured with a device placed in the right ventricle that penetrates the ventricular septum and emerges into the left ventricular cavity. This device may also have a pressure transducer that lies within the septal wall, and measures intra-septal force as a surrogate for contractility.

A blood pressure transducer 454 is located on either a separate blood pressure lead or as a separate sensor 456 on a ventricular lead 410. It is important to note that other blood pressure transduction devices may be incorporated into the device. Although BP measurement is preferred other BP proxy measurements may be substituted within the scope of the invention.

A blood pressure transducer is provided to measure blood pressure to determine the existence of hypertension. The blood pressure monitoring transducer may be located on a lead for example the RV ventricular lead or a separate BP lead may be provided.

It is expected that a BP algorithm will be developed which provides a BP threshold. The threshold may vary with time of day or patient activity. Once detected the stimulator will delivery a therapy for a treatment time. It is expected that the treatment time will be selected by the physician and it may be terminated automatically or it may time out. This episodic therapy may be used alone or in conjunction with a drug regime.

Proposed Mechanism of Action

It is believed that the present invention induces a controlled and temporary "inefficiency" in the mechanical function of the heart. This inefficiency is produced and controlled by altering either or all, the normal pacing rate, the normal electrical path of ionic gradient flow through the heart, or dyssynchronization between the right and left ventricles. In the normal heart, initiation of the heart beat occurs in the sinoatrial node that resides towards the epicardial surface of the right atrium close to the junction of the superior vena cava. Nodal cells have a constantly changing resting membrane potential measured in respect to the voltage difference between the outside and inside of the cell. There are protein channels that traverse the cardiac pacemaker cell membrane and allow ionic currents to flow across the membrane depending on channel opening and the diffusion gradient of various ions such as sodium, potassium and calcium. In the pacemaker cells, there are sodium and calcium channels that increase pacing rate by decreasing their resistance to ion flow from the outside to inside of the cell based on their diffusion gradients. These ions carry a positive charge thereby inducing a decrease in the resting membrane potential and make the cell less negative. As this process continues in time, the cell membrane reaches an activation voltage potential whereby the calcium channel opens completely, the doubly positively charged calcium ions flow into the cell causing a complete depolarization. This depolarization then conducts three dimensionally throughout the atrial contractile cells. Contractile cells differ from pacemaker cells in that they maintain a stable resting membrane potential by allowing a controlled amount of potassium ions to leave the cell, determined by the membrane potential. They also differ in that when they are confronted with either a positively charged depolarization wavefront or an artificially induced electrical stimulus, a sodium channel, instead of a calcium channel, is activated and the cell becomes depolarized. The depolarization in a contractile muscle cell then allows calcium ions to be release intracellularly from the sarcoplasmic reticulum and a cell contraction occurs.

When the depolarization wavefront of positive charges reaches the atrioventricular node, those cells become depolarized and the unidirectional wavefront continues down the "bundle of his" to the apex of the ventricles. Purkinje fibers rapidly conduct this depolarization wavefront away from the apex and into the muscle cells of the ventricles leading towards the base of the heart. The natural pathway of electrical conduction from the apex towards the base also results in a slight spiraling pathway. This allows the ventricular muscle to effectively and efficiently "wring" out blood from the chambers.

By implanting electrical stimulating leads in the ventricular chambers, the present invention allows for an artificial activation of the ventricular multidirectional depolarization wavefront. If the electrical stimulation leads are placed in the apex of the ventricles, a close approximation of the natural pathway of electrical-mechanical coupling occurs. If the pacing rate however is overdriven higher than the normal pacing rate, there will be less time for filling of blood into the chambers driven by the venous side filling pressure. In accordance with Starling's Law, less blood filling the chamber results in less stretch on the actin and myosin contractile filaments, and therefore less contractile force developed to eject blood from the chambers. Less ejection volume and ventricular pressure consequently results in less systemic blood pressure developed.

This invention also allows for de-synchronizing the right and left ventricular chambers. The stimulation leads may be placed in one or both of the ventricular apices and stimulated in a fashion that allows one chamber to contract prior to the other. Because the right ventricle anatomically wraps around the left ventricle and produces a chamber containing part of the left ventricle wall, a dyssynchronous contraction between the right and left chambers results in an inefficiency in mechanical function and resultant ejection of blood, initially from the right ventricle that results in less filling in the left ventricle and less ejection and lowered systemic blood pressure. Another aspect to this invention is the deliberate activation of single or multiple pacing sites in the ventricle (s) at locations other than the apex. Initiation of contraction at sites towards the base of the chamber results in myocardial contraction forces being applied to intra-chamber retrograde movement of blood and static pressure development in the apical part of the chamber. This force can be directly subtracted from the overall force developed by the ventricle to ejecting blood into the systemic circulation, resulting in lowered blood pressure.

What is claimed is:

1. A method, carried out with an implanted heart muscle stimulator associated with a heart of a patient, for treating a blood pressure disorder in the patient, the method comprising:
    using a sensor to measure the patient's pretreatment blood pressure corresponding to a pretreatment cardiac ejection profile;
    comparing the measured pretreatment blood pressure with a treatment threshold; and
    when the measured pretreatment blood pressure exceeds the treatment threshold, stimulating the patient's heart with an electrical stimulus timed relative to the patient's cardiac ejection cycle to cause dyssynchrony between at least two cardiac chambers and alter the patient's cardiac ejection profile from the pretreatment cardiac ejection profile, thereby reducing the patient's blood pressure from the measured pretreatment blood pressure.

2. The method of claim 1, wherein the dyssynchrony comprises an alteration of a pretreatment contraction sequence between the at least two cardiac chambers.

3. The method of claim 2, wherein the dyssynchrony comprises an alteration of a pretreatment contraction sequence between the at least two cardiac chambers that provides a reduced atrioventricular delay.

4. The method of claim 3, wherein the reduced atrioventricular delay disturbs the spatial contraction sequence between an atrial chamber and a ventricular chamber.

5. The method of claim 3, wherein the reduced atrioventricular delay disturbs the temporal contraction sequence between an atrial chamber and a ventricular chamber.

6. The method of claim 1, wherein the dyssynchrony comprises an alteration of a pretreatment contraction sequence between right and left ventricles of the patient's heart.

7. The method of claim 1, wherein the patient's heart is stimulated on a beat-by-beat interval.

8. The method of claim 1, wherein the patient's heart is stimulated at a pacing rate above sinus rhythm.

9. The method of claim 1, wherein the patient's heart is stimulated at a pacing rate within a range of approximately 90 to approximately 100 beats per minute.

10. The method of claim 1, wherein the patient's heart is stimulated at a burst pacing rate to approximately 300 beats per minute.

11. The method of claim 1, wherein the electrical stimulus comprises a pacing level stimulus that alters the patient's cardiac ejection profile for an individual heartbeat.

12. A method, carried out with an implanted heart muscle stimulator associated with a heart of a patient, for treating a blood pressure disorder in the patient, comprising:
    using a sensor to measure the patient's pretreatment blood pressure corresponding to a pretreatment cardiac ejection profile;
    comparing the measured pretreatment blood pressure with a treatment threshold; and
    when the measured pretreatment blood pressure exceeds the treatment threshold, stimulating the patient's heart with an electrical stimulus timed relative to the patient's cardiac ejection cycle to cause a dyssynchronous timing between at least two cardiac chambers and alter the patient's cardiac ejection profile from the pretreatment cardiac ejection profile, thereby reducing the patient's blood pressure from the measured pretreatment blood pressure.

13. The method of claim 12, wherein the dyssynchronous timing comprises an alteration of a pretreatment contraction sequence between atrial and ventricular chambers.

14. The method of claim 13, wherein stimulating the patient's heart comprises stimulating atrial and ventricular chambers of the patient's heart.

15. The method of claim 13, wherein the alteration of the pretreatment contraction sequence between the atrial and ventricular chambers comprises a reduced atrioventricular delay.

16. The method of claim 15, wherein the reduced atrioventricular delay disturbs the spatial contraction sequence between the atrial and ventricular chambers.

17. The method of claim 15, wherein the reduced atrioventricular delay disturbs the temporal contraction sequence between the atrial and ventricular chambers.

18. The method of claim 12, wherein the patient's heart is stimulated on a beat-by-beat interval.

19. The method of claim 12, wherein the patient's heart is stimulated at a pacing rate above sinus rhythm.

20. The method of claim 12, wherein the patient's heart is stimulated at a pacing rate within a range of approximately 90 to approximately 100 beats per minute.

21. The method of claim 12, wherein the patient's heart is stimulated at a burst pacing rate to approximately 300 beats per minute.

22. The method of claim 12, wherein the electrical stimulus comprises a pacing level stimulus that alters the patient's cardiac ejection profile for an individual heartbeat.

* * * * *